US010683537B2

(12) United States Patent
Kermekchiev et al.

(10) Patent No.: US 10,683,537 B2
(45) Date of Patent: Jun. 16, 2020

(54) INHIBITION-RESISTANT POLYMERASES

(71) Applicant: DNA Polymerase Technology, Inc., St. Louis, MO (US)

(72) Inventors: Milko B. Kermekchiev, St. Louis, MO (US); Zhian Zhang, Ballwin, MO (US)

(73) Assignee: DNA Polymerase Technology, Inc., St. Louis, MO (US)

( * ) Notice: Subject to any disclaimer, the term of this patent is extended or adjusted under 35 U.S.C. 154(b) by 0 days.

(21) Appl. No.: 14/055,796

(22) Filed: Oct. 16, 2013

(65) Prior Publication Data

US 2014/0113299 A1 Apr. 24, 2014

Related U.S. Application Data

(60) Provisional application No. 61/811,611, filed on Apr. 12, 2013, provisional application No. 61/714,671, filed on Oct. 16, 2012.

(51) Int. Cl.
*C12Q 1/686* (2018.01)
*C12N 9/12* (2006.01)

(52) U.S. Cl.
CPC ........... *C12Q 1/686* (2013.01); *C12N 9/1252* (2013.01)

(58) Field of Classification Search
CPC . C12C 1/686; C12C 2521/101; C12N 9/1252; C12N 15/1096; C12N 9/1276; C12Q 1/686; C12Q 2521/101; C12Q 1/6846; C12Q 2531/101; C12Q 2531/119; C12Q 2521/107; C12Q 2527/101; C12Q 2549/101; C12Q 2549/107; C12Y 207/07007; C12Y 207/07049
See application file for complete search history.

(56) References Cited

U.S. PATENT DOCUMENTS

| 5,436,149 | A |   | 7/1995 | Barnes |
|---|---|---|---|---|
| 5,436,326 | A |   | 7/1995 | Ishino et al. |
| 5,616,494 | A | * | 4/1997 | Barnes ................ C12N 9/1252 |
|   |   |   |   | 435/194 |
| 5,753,482 | A |   | 5/1998 | Ishino et al. |
| 5,928,866 | A |   | 7/1999 | Imamoto et al. |
| 6,210,885 | B1 |   | 4/2001 | Gjerde et al. |
| 6,395,526 | B1 |   | 5/2002 | Uemori et al. |

(Continued)

FOREIGN PATENT DOCUMENTS

| CN | 103266103 | 8/2013 |
|---|---|---|
| JP | 2009136188 | 6/2009 |

(Continued)

OTHER PUBLICATIONS

Ong et al. (Directed Evolution of DNA Polymerase, RNA Polymerase and Reverse Transcriptase Activity in a Single Polypeptide, J Mol Biol. Aug. 18, 2006;361(3):537-50. Epub Jul. 5, 2006).*

(Continued)

*Primary Examiner* — Randall L Beane
(74) *Attorney, Agent, or Firm* — Stinson LLP

(57) ABSTRACT

Provided herein are mutant polymerase enzymes resistant to inhibitors encountered in Polymerase Chain Reactions (PCR). Also provided are nucleic acids or constructs encoding isolated polypeptides having polymerase activity. Also provided are kits useful for PCR containing isolated polypeptides having polymerase activity or isolated nucleic acids encoding such.

20 Claims, 13 Drawing Sheets

Specification includes a Sequence Listing.

Resistance of New Full-Length Taq Mutant C66 to Shrimp Meat Inhibition

(56) References Cited

U.S. PATENT DOCUMENTS

| | | | |
|---|---|---|---|
| 6,410,277 | B1 | 6/2002 | Barnes |
| 6,448,048 | B1 | 9/2002 | Tomono et al. |
| 7,211,647 | B2 | 5/2007 | Ishino et al. |
| 7,393,635 | B2 | 7/2008 | Barnes |
| 7,462,475 | B2* | 12/2008 | Kermekchiev ........ C12Q 1/686 435/183 |
| 7,820,423 | B2 | 10/2010 | Doi et al. |
| 7,927,853 | B2 | 4/2011 | Nishida et al. |
| 8,003,346 | B2 | 8/2011 | Tokida et al. |
| 8,481,685 | B2 | 7/2013 | Bourne et al. |
| 9,796,965 | B2* | 10/2017 | Kermekchiev ........ C12Q 1/686 |
| 2004/0005594 | A1* | 1/2004 | Holliger ............... C12N 9/1252 435/6.16 |
| 2004/0081963 | A1* | 4/2004 | Wang .................... C12N 9/1252 435/6.11 |
| 2005/0250131 | A1* | 11/2005 | Jestin et al. ....................... 435/6 |
| 2006/0084074 | A1 | 4/2006 | Kermekchiev et al. |
| 2007/0020622 | A1 | 1/2007 | Lee et al. |
| 2007/0048748 | A1* | 3/2007 | Williams et al. .................. 435/6 |
| 2008/0014609 | A1* | 1/2008 | Jestin ............... C07K 14/43563 435/69.1 |
| 2008/0166772 | A1* | 7/2008 | Hollinger et al. ........... 435/91.2 |
| 2009/0170060 | A1* | 7/2009 | Kermekchiev et al. .......... 435/2 |
| 2011/0027832 | A1 | 2/2011 | Kermekchiev et al. |
| 2011/0027833 | A1 | 2/2011 | Hogrefe et al. |
| 2011/0142792 | A1* | 6/2011 | Kahre .................... C07K 14/00 424/85.1 |
| 2011/0281305 | A1* | 11/2011 | Bourn .................. C12N 9/1241 435/91.2 |
| 2012/0028259 | A1 | 2/2012 | Zhang et al. |
| 2012/0094332 | A1 | 4/2012 | Lee et al. |
| 2013/0034879 | A1 | 2/2013 | Skirgaila et al. |
| 2013/0040365 | A1* | 2/2013 | Vander Horn ....... C12Q 1/6846 435/194 |
| 2013/0209473 | A1 | 8/2013 | de Sauvage et al. |
| 2014/0113299 | A1 | 4/2014 | Kermekchiev et al. |
| 2014/0186840 | A1* | 7/2014 | Ding .................... C12N 9/1252 435/6.12 |
| 2014/0322793 | A1 | 10/2014 | Ishino et al. |
| 2014/0363875 | A1 | 12/2014 | Ishino et al. |

FOREIGN PATENT DOCUMENTS

| | | |
|---|---|---|
| WO | WO1992006200 | 4/1992 |
| WO | WO2005113829 | 12/2005 |
| WO | WO 2010/062777 A2 | 6/2010 |
| WO | WO 2010/062779 A2 | 6/2010 |
| WO | WO 2012/088479 A2 | 6/2012 |
| WO | WO2014181875 | 11/2014 |
| WO | 2016/183294 A1 | 11/2016 |

OTHER PUBLICATIONS

Kermekchiev et al. (Mutants of Taq DNA polymerase resistant to PCR inhibitors allow DNA amplification from whole blood and crude soil samples, Nucl. Acids Res. (2009) 37 (5): e40. First published online: Feb. 10, 2009).*
Steitz, The J. of Biol. Chem., vol. 274(25):17395-17398 (Jun. 18, 1999).*
Livingstone et al., CABIOS, vol. 9(6):745-756 (1993).*
AAA27507.1, DNA polymerase [Thermus aquaticus], GenBank: AAA27507.1, NCBI.nlm.gov, 3 pages (Apr. 26, 1993).*
Higuchi et al., Kinetic PCR Analysis: Real-time Monitoring of DNA Amplification Reactions, Nature Bio/Technology, vol. 11:1026-1030 (Sep. 1993).*
Dillon et al., RNA as an Experimental and Therapeutic Tool to Study and Regulate Physiological and Disease Processes, Ann. Rev. Physiol., 2005, pp. 147-173, vol. 67.
Dykxhoorn et al., The Silent Revolution: RNA Interference as Basic Biology, Research Tool, and Therapeutic, Annu. Rev. Med., 2005, pp. 401-423, vol. 56.
Elhai et al., Conjugal Transfer of DNA to Cyanobacteria, Methods in Enzymology, 1988, pp. 747-754, vol. 167.
Ghadessy et al., Directed evolution of polymerase function by compartmentalized self-replication, PNAS, 2001, pp. 4552-4557, vol. 98, No. 8.
Helene et al., Control of Gene Expression by Triple Helix-Forming Oligonucleotides, Ann. N.Y. Acad. Sci., 1992, pp. 27-36, vol. 660.
International Search Report and Written Opinion dated Feb. 4, 2014 in corresponding International Application No. PCT/US2013/065313 filed Oct. 16, 2012, 9 pages.
Kermekchiev et al., Mutants of Taq DNA polymerase resistant to PCR inhibitors allow DNA amplification from whole blood and crude soil samples, Nucleic Acids Research, 2009, e40, pp. 1-14, vol. 37, No. 5.
Lawyer et al., Isolation, Characterization, and Expression in *Escherichia coli* of the DNA Polymerase Gene from *Thermus aquaticus*, J Biological Chemistry, 1989, pp. 6427-6437, vol. 264, No. 11.
Lee et al., Aptamer Therapeutics Advance, Current Opinion in Chemical Biology, 2006, pp. 282-289, vol. 10.
Link et al., Beyond toothpicks: new methods for isolating mutant bacteria, Nature Reviews, 2007, pp. 680-688, vol. 5.
Maher, III, DNA Triple-Helix Formation: An Approach to Artificial Gene Repressors?, BioEssays, 1992, pp. 807-815, vol. 14, No. 12.
Ong et al., Directed Evolution of DNA Polymerase, RNA Polymerase and Reverse Transcriptase Activity in a Single Polypeptide, J. Mol. Biol., 2006, pp. 537-550, vol. 361.
Pushparaj et al., Short Interfering RNA (siRNA) as a Novel Therapeutic, Clin. and Exper. Pharma. and Physiol., 2006, pp. 504-510, vol. 33.
Reynolds et al., Rational siRNA design for RNA interference, Nature Biotechnology, 2004, pp. 326-330, vol. 22, No. 3.
Sagner et al., Rapid filter assay for the detection of DNA polymerase activity: direct identification of the gene for the DNA polymerase from Thermus aquaticus, Gene, 1991, pp. 119-123, vol. 97.
Studier, Protein production by auto-induction in high-density shaking cultures, Protein Expression and Purification, 2005, pp. 207-234, vol. 41.
Europe Supplementary Partial Search Report dated Apr. 26, 2016 in related Application No. 13847958.9 filed Oct. 16, 2013 (8 pages).
Kermekchiev, M. B., et al., "Cold-Sensitive Mutants of Taq DNA Polymerase Provide a Hot Start for PCR," Nucleic Acids Research, 2003, pp. 6139-6147, vol. 31, No. 21.
Ederth, J., et al., "Functional Interplay Between the Jaw Domain of Bacterial RNA Polymerase and Allele-Specific Residues in the Product RNA-Binding Pocket," Journal of Molecular Biology, 2006, pp. 1163-1179, vol. 356, No. 5.
Berg, K. A., et al., "A Conservative, Single-Amino Acid Substitution in the Second Cytoplasmic Domain of the Human Serotonin2C Receptor Alters Both Ligand-Dependent and -Independent Receptor Signaling," The Journal of Pharmacology and Experimental Therapeutics, 2008, pp. 1084-1092, vol. 324, No. 3.
Jonson, H., et al., "A Critical View on Conservative Mutations," Protein Engineering, 2001, pp. 397-402, vol. 14, No. 6.
Seshu, J., et al., "A Conservative Amino Acid Change Alters the Function of BosR, The Redox Regulator of Borrelia burgdorferi," Molecular Microbiology, 2004, pp. 1352-1363, vol. 54, No. 5.
Summers, R. G., et al., "A Conservative Amino Acid Substitution, Arginine for Lysine, Abolishes Export of a Hybrid Protein in *Escherichia coli*," The Journal of Biological Chemistry, Nov. 1989, pp. 20082-20088, vol. 264, No. 33.
Wu, E. Y., et al., "A Conservative Isoleucin to Leucine Mutation Causes Major Rearrangements and Cold Sensitivity in KlenTaq(sup1) DNA Polymerase," Biochemistry, 2015, pp. 881-889, vol. 54.

* cited by examiner

Resistance of Klentaq mutants to bile inhibition

SEQUENCE LISTING

<160> NUMBER OF SEQ ID NOS: 14

<210> SEQ ID NO 1
<211> LENGTH: 832
<212> TYPE: PRT
<213> ORGANISM: Thermus aquaticus

<400> SEQUENCE: 1

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

Ala Leu Ile Lys Glu Leu Val Asp Leu Leu Gly Leu Ala Arg Leu Glu
        100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
            165                 170                 175

Asp Gln Trp Ala Asp Tyr Arg Ala Leu Thr Gly Asp Glu Ser Asp Asn
        180                 185                 190

Leu Pro Gly Val Lys Gly Ile Gly Glu Lys Thr Ala Arg Lys Leu Leu
    195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
    355                 360                 365
```

```
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
770                 775                 780
Asp Glu Leu Val Leu Glu Ala Pro Lys Glu Arg Ala Glu Ala Val Ala
```

785                 790                 795                 800
Arg Leu Ala Lys Glu Val Met Glu Gly Val Tyr Pro Leu Ala Val Pro
                    805                 810                 815
Leu Glu Val Glu Val Gly Ile Gly Glu Asp Trp Leu Ser Ala Lys Glu
                820                 825                 830

<210> SEQ ID NO 2
<211> LENGTH: 554
<212> TYPE: PRT
<213> ORGANISM: Thermus aquaticus

<400> SEQUENCE: 2

Met Gly Leu Leu His Glu Phe Gly Leu Leu Glu Ser Pro Lys Ala Leu
1               5                   10                  15

Glu Glu Ala Pro Trp Pro Pro Gly Ala Phe Val Gly Phe Val
                20                  25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
        50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

```
Glu Leu Arg Val Leu Ala His Leu Ser Gly Asp Glu Asn Leu Ile Arg
                340                 345                 350

Val Phe Gln Glu Gly Arg Asp Ile His Thr Glu Thr Ala Ser Trp Met
            355                 360                 365

Phe Gly Val Pro Arg Glu Ala Val Asp Pro Leu Met Arg Arg Ala Ala
        370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
            420                 425                 430

Leu Glu Glu Gly Arg Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
530                 535                 540

Ile Gly Glu Asp Trp Leu Ser Ala Lys Glu
545                 550

<210> SEQ ID NO 3
<211> LENGTH: 832
<212> TYPE: PRT
<213> ORGANISM: Thermus aquaticus

<400> SEQUENCE: 3

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160
```

```
Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575
```

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
            610                 615                 620

Asp Lys Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Leu Asn Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 4
<211> LENGTH: 554
<212> TYPE: PRT
<213> ORGANISM: Thermus aquaticus

<400> SEQUENCE: 4

Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
                20                  25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
        50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

```
Ala Leu Ser Glu Arg Leu Phe Ala Asn Leu Trp Gly Arg Leu Glu Gly
            130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
                180                 185                 190

Glu Ala Glu Val Phe Arg Leu Ala Gly His Pro Phe Asn Leu Asn Ser
            195                 200                 205

Arg Asp Gln Leu Glu Arg Val Leu Phe Asp Glu Leu Gly Leu Pro Ala
210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
                260                 265                 270

Asp Leu Ile His Pro Arg Thr Gly Arg Leu His Thr Arg Phe Asn Gln
                275                 280                 285

Thr Ala Thr Ala Thr Gly Arg Leu Ser Ser Ser Asp Pro Asn Leu Gln
            290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Lys Asn Leu Ile Arg
                340                 345                 350

Val Phe Gln Glu Gly Arg Asp Ile His Thr Glu Thr Ala Ser Trp Met
            355                 360                 365

Phe Gly Val Pro Arg Glu Ala Val Asp Pro Leu Met Arg Arg Ala Ala
            370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Leu Lys Lys Thr
                420                 425                 430

Leu Glu Glu Gly Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
            515                 520                 525

Met Glu Gly Val Tyr Pro Leu Ala Val Pro Leu Glu Val Glu Val Gly
            530                 535                 540
```

```
Ile Gly Glu Asp Trp Leu Ser Ala Lys Glu
545                 550
```

<210> SEQ ID NO 5
<211> LENGTH: 554
<212> TYPE: PRT
<213> ORGANISM: Thermus aquaticus

<400> SEQUENCE: 5

```
Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
            20                  25                  30

Leu Ser Arg Lys Glu Pro Met Trp Ala Asp Leu Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205

Gly Asp Gln Leu Glu Arg Val Leu Phe Asp Glu Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
            340                 345                 350

Val Phe Gln Glu Gly Arg Asp Ile His Thr Glu Thr Ala Ser Trp Met
        355                 360                 365
```

```
Phe Gly Val Pro Arg Glu Ala Val Asp Pro Leu Met Arg Ala Ala
        370                 375                 380

Lys Thr Ile Asn Phe Val Leu Tyr Gly Met Ser Ala His Arg Leu
385                 390                 395                 400

Ser Gln Glu Leu Ala Ile Pro Tyr Glu Ala Gln Ala Phe Ile Glu
                405                 410                 415

Arg Tyr Phe Gln Ser Phe Pro Lys Val Arg Ala Trp Ile Glu Lys Thr
                420                 425                 430

Leu Glu Glu Gly Arg Arg Gly Tyr Val Glu Thr Leu Phe Gly Arg
                435                 440                 445

Arg Arg Tyr Val Pro Asp Leu Glu Ala Arg Val Lys Ser Val Arg Glu
450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
                500                 505                 510

Ala Pro Lys Glu Arg Ala Glu Ala Val Ala Arg Leu Ala Lys Glu Val
                515                 520                 525

Met Glu Gly Val Tyr Pro Leu Ala Val Pro Leu Glu Val Glu Val Gly
                530                 535                 540

Ile Gly Glu Asp Trp Leu Ser Ala Lys Glu
545                 550

<210> SEQ ID NO 6
<211> LENGTH: 554
<212> TYPE: PRT
<213> ORGANISM: Thermus aquaticus

<400> SEQUENCE: 6

Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
                20                  25                  30

Leu Ser Arg Lys Glu Pro Met Trp Ala Asp Leu Leu Ala Leu Ala Ala
                35                  40                  45

Ala Arg Gly Gly Arg Val His Arg Ala Pro Glu Pro Tyr Lys Ala Leu
            50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Ala Gly Glu Arg Ala
            115                 120                 125

Ala Leu Ser Glu Arg Leu Phe Ala Asn Leu Trp Glu Arg Leu Glu Gly
        130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
```

```
            180                 185                 190
Glu Ala Glu Val Phe Arg Leu Ala Gly His Pro Phe Asn Leu Asn Ser
            195                 200                 205
Arg Asp Gln Leu Glu Arg Val Leu Phe Asp Glu Leu Gly Leu Pro Ala
            210                 215                 220
Ile Gly Lys Thr Glu Lys Thr Gly Lys Arg Ser Thr Ser Ala Ala Val
225                 230                 235                 240
Leu Glu Ala Leu Arg Glu Ala His Pro Ile Val Glu Lys Ile Leu Gln
            245                 250                 255
Tyr Arg Glu Leu Thr Lys Leu Lys Ser Thr Tyr Ile Asp Pro Leu Pro
            260                 265                 270
Asp Leu Ile His Pro Arg Thr Gly Arg Leu His Thr Arg Phe Asn Gln
            275                 280                 285
Thr Ala Thr Ala Thr Gly Arg Leu Ser Ser Ser Asp Pro Asn Leu Gln
            290                 295                 300
Asn Ile Pro Val Arg Thr Pro Leu Gly Gln Arg Ile Arg Arg Ala Phe
305                 310                 315                 320
Ile Ala Glu Glu Gly Trp Leu Leu Val Ala Leu Asp Tyr Ser Gln Ile
            325                 330                 335
Glu Leu Arg Val Leu Ala His Leu Ser Gly Asp Lys Asn Leu Ile Arg
            340                 345                 350
Val Phe Gln Glu Gly Arg Asp Ile His Thr Glu Thr Ala Ser Trp Met
            355                 360                 365
Phe Gly Val Pro Arg Glu Ala Val Asp Pro Leu Met Arg Arg Ala Ala
370                 375                 380
Lys Thr Ile Asn Phe Gly Val Leu Tyr Gly Met Ser Ala His Arg Leu
385                 390                 395                 400
Ser Gln Glu Leu Ala Ile Pro Tyr Glu Glu Ala Gln Ala Phe Ile Glu
            405                 410                 415
Arg Tyr Phe Gln Ser Phe Pro Lys Val Arg Ala Trp Leu Ser Lys Thr
            420                 425                 430
Leu Glu Glu Gly Arg Arg Gly Tyr Val Glu Thr Leu Phe Gly Arg
            435                 440                 445
Arg Arg Tyr Val Pro Asp Leu Glu Ala Arg Val Lys Ser Val Arg Glu
            450                 455                 460
Ala Ala Glu Arg Met Ala Phe Asn Met Pro Val Gln Gly Thr Ala Ala
465                 470                 475                 480
Asp Leu Met Lys Leu Ala Met Val Lys Leu Phe Pro Arg Leu Glu Glu
            485                 490                 495
Met Gly Ala Arg Met Leu Leu Gln Val His Asp Glu Leu Val Leu Glu
            500                 505                 510
Ala Pro Lys Glu Arg Ala Glu Ala Val Ala Arg Leu Ala Lys Glu Val
            515                 520                 525
Met Glu Gly Val Tyr Pro Leu Ala Val Pro Leu Glu Val Glu Val Gly
            530                 535                 540
Ile Gly Glu Asp Trp Leu Ser Ala Lys Glu
545                 550

<210> SEQ ID NO 7
<211> LENGTH: 554
<212> TYPE: PRT
<213> ORGANISM: Thermus aquaticus

<400> SEQUENCE: 7
```

```
Met Gly Leu Leu His Glu Phe Gly Leu Leu Glu Ser Pro Lys Ala Leu
1               5                   10                  15

Glu Glu Ala Pro Trp Pro Pro Gly Ala Phe Val Gly Phe Val
            20              25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
            50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Glu Ala Gly Glu Arg Ala
            115                 120                 125

Ala Leu Ser Glu Arg Leu Phe Ala Asn Leu Trp Gly Arg Leu Glu Gly
            130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Ile Ala Arg Leu
                180                 185                 190

Glu Ala Glu Val Phe Arg Leu Ala Gly His Pro Phe Asn Leu Asn Ser
            195                 200                 205

Arg Asp Gln Leu Glu Arg Val Leu Phe Asp Glu Leu Gly Leu Pro Ala
            210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Arg Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
            275                 280                 285

Thr Ala Thr Ala Thr Gly Arg Leu Ser Ser Ser Asp Pro Asn Leu Gln
            290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
                340                 345                 350

Val Phe Gln Glu Gly Arg Asp Ile His Thr Glu Thr Ala Ser Trp Met
            355                 360                 365

Phe Gly Val Pro Arg Glu Ala Val Asp Pro Leu Met Arg Arg Ala Ala
370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
```

```
            420                 425                 430
Leu Glu Glu Gly Arg Arg Gly Tyr Val Glu Thr Leu Phe Gly Arg
            435                 440                 445

Arg Arg Tyr Val Pro Asp Leu Glu Ala Arg Val Lys Ser Val Arg Glu
            450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
                500                 505                 510

Ala Pro Lys Glu Arg Ala Glu Ala Val Ala Arg Leu Ala Lys Glu Val
                515                 520                 525

Met Glu Gly Val Tyr Pro Leu Ala Val Pro Leu Glu Val Glu Val Gly
                530                 535                 540

Ile Gly Glu Asp Trp Leu Ser Ala Lys Glu
545                 550

<210> SEQ ID NO 8
<211> LENGTH: 554
<212> TYPE: PRT
<213> ORGANISM: Thermus aquaticus

<400> SEQUENCE: 8

Met Gly Leu Leu His Glu Phe Gly Leu Leu Glu Ser Pro Lys Ala Leu
1               5                   10                  15

Glu Glu Ala Pro Trp Pro Pro Pro Glu Gly Ala Phe Val Gly Phe Val
                20                  25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
        50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
                100                 105                 110

Ala Arg Arg Tyr Gly Gly Glu Trp Thr Glu Glu Ala Gly Glu Arg Ala
            115                 120                 125

Ala Leu Ser Glu Arg Leu Phe Ala Asn Leu Trp Gly Arg Leu Glu Gly
        130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Val Ala
                165                 170                 175

Tyr Leu Arg Ala Leu Ser Leu Glu Val Ala Glu Glu Ile Ala Arg Leu
                180                 185                 190

Glu Ala Glu Val Phe Arg Leu Ala Gly His Pro Phe Asn Leu Asn Ser
            195                 200                 205

Arg Asp Gln Leu Glu Arg Val Leu Phe Asp Glu Leu Gly Leu Pro Ala
        210                 215                 220

Ile Gly Lys Thr Glu Lys Thr Gly Lys Arg Ser Thr Ser Ala Ala Val
225                 230                 235                 240
```

```
Leu Glu Ala Leu Arg Glu Ala His Pro Ile Val Glu Lys Ile Leu Gln
            245                 250                 255

Tyr Arg Glu Leu Thr Lys Leu Lys Ser Thr Tyr Ile Asp Pro Leu Pro
        260                 265                 270

Asp Leu Ile His Pro Arg Thr Gly Arg Leu His Thr Arg Phe Asn Gln
            275                 280                 285

Thr Ala Thr Ala Thr Gly Arg Leu Ser Ser Ser Asp Pro Asn Leu Gln
290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
    370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
            420                 425                 430

Leu Glu Glu Gly Arg Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
    450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Ile Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
    530                 535                 540

Ile Gly Glu Asp Trp Leu Ser Ala Lys Glu
545                 550

<210> SEQ ID NO 9
<211> LENGTH: 832
<212> TYPE: PRT
<213> ORGANISM: Thermus aquaticus

<400> SEQUENCE: 9

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60
```

```
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
                115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480
```

```
Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Glu Pro Asn Leu Gln Asn Ile Pro Val Arg Thr Pro Leu Gly Gln
            580                 585                 590

Arg Ile Arg Arg Ala Phe Ile Ala Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 10
<211> LENGTH: 832
<212> TYPE: PRT
<213> ORGANISM: Thermus aquaticus

<400> SEQUENCE: 10

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30
```

```
Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445
```

```
Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Gly Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Val Ala Glu Glu Gly Trp Leu Leu Val Ala
            595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Gln Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830
```

<210> SEQ ID NO 11
<211> LENGTH: 832
<212> TYPE: PRT
<213> ORGANISM: Thermus aquaticus

<400> SEQUENCE: 11

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

-continued

```
Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440             445

Val Arg Leu Asp Val Ala Tyr Leu Arg Ala Leu Ser Leu Glu Val Ala
        450                 455                 460

Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Val Val Glu Val Gly Ile Gly Glu Asp Trp Leu Ser Ala Lys Glu
            820                 825                 830
```

<210> SEQ ID NO 12
<211> LENGTH: 832
<212> TYPE: PRT
<213> ORGANISM: Thermus aquaticus

<400> SEQUENCE: 12

| | | | | | | | | | | | | | | |
|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | His | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | | 35 | | | | 40 | | | | | 45 | | | |
| Lys | Ser | Leu | Leu | Lys | Ala | Leu | Lys | Glu | Asp | Gly | Asp | Ala | Val | Ile | Val |
| 50 | | | | | 55 | | | | | 60 | | | | | |
| Val | Phe | Asp | Ala | Lys | Ala | Pro | Ser | Phe | Arg | His | Glu | Ala | Tyr | Gly | Gly |
| 65 | | | | | 70 | | | | | 75 | | | | | 80 |
| Tyr | Lys | Ala | Gly | Arg | Ala | Pro | Thr | Pro | Glu | Asp | Phe | Pro | Arg | Gln | Leu |
| | | | | 85 | | | | | 90 | | | | | 95 | |
| Ala | Leu | Ile | Lys | Glu | Leu | Val | Asp | Leu | Leu | Gly | Leu | Ala | Arg | Leu | Glu |
| | | | 100 | | | | | 105 | | | | | 110 | | |
| Val | Pro | Gly | Tyr | Glu | Ala | Asp | Asp | Val | Leu | Ala | Ser | Leu | Ala | Lys | Lys |
| | | | 115 | | | | | 120 | | | | | 125 | | |
| Ala | Glu | Lys | Glu | Gly | Tyr | Glu | Val | Arg | Ile | Leu | Thr | Ala | Asp | Lys | Asp |
| | 130 | | | | | 135 | | | | | 140 | | | | |
| Leu | Tyr | Gln | Leu | Leu | Ser | Asp | Arg | Ile | His | Val | Leu | His | Pro | Glu | Gly |
| 145 | | | | | 150 | | | | | 155 | | | | | 160 |
| Tyr | Leu | Ile | Thr | Pro | Ala | Trp | Leu | Trp | Glu | Lys | Tyr | Gly | Leu | Arg | Pro |
| | | | | 165 | | | | | 170 | | | | | 175 | |
| Asp | Gln | Trp | Ala | Asp | Tyr | Arg | Ala | Leu | Thr | Gly | Asp | Glu | Ser | Asp | Asn |
| | | | 180 | | | | | 185 | | | | | 190 | | |
| Leu | Pro | Gly | Val | Lys | Gly | Ile | Gly | Glu | Lys | Thr | Ala | Arg | Lys | Leu | Leu |
| | | | | 195 | | | | | 200 | | | | | 205 | |
| Glu | Glu | Trp | Gly | Ser | Leu | Glu | Ala | Leu | Leu | Lys | Asn | Leu | Asp | Arg | Leu |
| | 210 | | | | | 215 | | | | | 220 | | | | |
| Lys | Pro | Ala | Ile | Arg | Glu | Lys | Ile | Leu | Ala | His | Met | Asp | Asp | Leu | Lys |
| 225 | | | | | 230 | | | | | 235 | | | | | 240 |
| Leu | Ser | Trp | Asp | Leu | Ala | Lys | Val | Arg | Thr | Asp | Leu | Pro | Leu | Glu | Val |
| | | | | 245 | | | | | 250 | | | | | 255 | |
| Asp | Phe | Ala | Lys | Arg | Arg | Glu | Pro | Asp | Arg | Glu | Arg | Leu | Arg | Ala | Phe |
| | | | 260 | | | | | 265 | | | | | 270 | | |
| Leu | Glu | Arg | Leu | Glu | Phe | Gly | Ser | Leu | Leu | His | Glu | Phe | Gly | Leu | Leu |
| | | | | 275 | | | | | 280 | | | | | 285 | |
| Glu | Ser | Pro | Lys | Ala | Leu | Glu | Glu | Ala | Pro | Trp | Pro | Pro | Pro | Glu | Gly |
| | 290 | | | | | 295 | | | | | 300 | | | | |
| Ala | Phe | Val | Gly | Phe | Val | Leu | Ser | Arg | Lys | Glu | Pro | Met | Trp | Ala | Asp |
| 305 | | | | | 310 | | | | | 315 | | | | | 320 |
| Leu | Leu | Ala | Leu | Ala | Ala | Ala | Arg | Gly | Gly | Arg | Val | His | Arg | Ala | Pro |
| | | | | 325 | | | | | 330 | | | | | 335 | |
| Glu | Pro | Tyr | Lys | Ala | Leu | Arg | Asp | Leu | Lys | Glu | Ala | Arg | Gly | Leu | Leu |
| | | | 340 | | | | | 345 | | | | | 350 | | |
| Ala | Lys | Asp | Leu | Ser | Val | Leu | Ala | Leu | Arg | Glu | Gly | Leu | Gly | Leu | Pro |
| | | | | 355 | | | | | 360 | | | | | 365 | |
| Pro | Gly | Asp | Asp | Pro | Met | Leu | Leu | Ala | Tyr | Leu | Leu | Asp | Pro | Ser | Asn |
| | 370 | | | | | 375 | | | | | 380 | | | | |

-continued

```
Thr Thr Pro Glu Gly Val Ala Arg Arg Tyr Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
        420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
    740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
```

Leu Glu Val Glu Val Gly Ile Gly Glu Asp Trp Leu Ser Ala Lys Glu
          805                 810                 815
Leu Glu Val Glu Val Gly Ile Gly Glu Asp Trp Leu Ser Ala Lys Glu
          820                 825                 830

<210> SEQ ID NO 13
<211> LENGTH: 816
<212> TYPE: PRT
<213> ORGANISM: Thermus aquaticus

<400> SEQUENCE: 13

Val Asp Gly His His Leu Ala Tyr Arg Thr Phe His Ala Leu Lys Gly
 1               5                  10                  15

Leu Thr Thr Ser Arg Gly Glu Pro Val Gln Ala Val Tyr Gly Phe Ala
             20                  25                  30

Lys Ser Leu Leu Lys Ala Leu Lys Glu Asp Gly Asp Ala Val Ile Val
         35                  40                  45

Val Phe Asp Ala Lys Ala Pro Ser Phe Arg His Glu Ala Tyr Gly Gly
     50                  55                  60

Tyr Lys Ala Gly Arg Ala Pro Thr Pro Glu Asp Phe Pro Arg Gln Leu
 65                  70                  75                  80

Ala Leu Ile Lys Glu Leu Val Asp Leu Gly Leu Ala Arg Leu Glu
                 85                  90                  95

Val Pro Gly Tyr Glu Ala Asp Asp Val Leu Ala Ser Leu Ala Lys Lys
            100                 105                 110

Ala Glu Lys Glu Gly Tyr Glu Val Arg Ile Leu Thr Ala Asp Lys Asp
        115                 120                 125

Leu Tyr Gln Leu Leu Ser Asp Arg Ile His Val Leu His Pro Glu Gly
    130                 135                 140

Tyr Leu Ile Thr Pro Ala Trp Leu Trp Glu Lys Tyr Gly Leu Arg Pro
145                 150                 155                 160

Asp Gln Trp Ala Asp Tyr Arg Ala Leu Thr Gly Asp Glu Ser Asp Asn
                165                 170                 175

Leu Pro Gly Val Lys Gly Ile Gly Glu Lys Thr Ala Arg Lys Leu Leu
            180                 185                 190

Glu Glu Trp Gly Ser Leu Glu Ala Leu Leu Lys Asn Leu Asp Arg Leu
        195                 200                 205

Lys Pro Ala Ile Arg Glu Lys Ile Leu Ala His Met Asp Asp Leu Lys
    210                 215                 220

Leu Ser Trp Asp Leu Ala Lys Val Arg Thr Asp Leu Pro Leu Glu Val
225                 230                 235                 240

Asp Phe Ala Lys Arg Arg Glu Pro Asp Arg Glu Arg Leu Arg Ala Phe
                245                 250                 255

Leu Glu Arg Leu Glu Phe Gly Ser Leu Leu His Glu Phe Gly Leu Leu
            260                 265                 270

Glu Ser Pro Lys Ala Leu Glu Glu Ala Pro Trp Pro Pro Pro Glu Gly
        275                 280                 285

Ala Phe Val Gly Phe Val Leu Ser Arg Lys Glu Pro Met Trp Ala Asp
    290                 295                 300

Leu Leu Ala Leu Ala Ala Ala Arg Gly Gly Arg Val His Arg Ala Pro
305                 310                 315                 320

Glu Pro Tyr Lys Ala Leu Arg Asp Leu Lys Glu Ala Arg Gly Leu Leu
                325                 330                 335

Ala Lys Asp Leu Ser Val Leu Ala Leu Arg Glu Gly Leu Gly Leu Pro
            340                 345                 350

-continued

```
Pro Gly Asp Asp Pro Met Leu Leu Ala Tyr Leu Leu Asp Pro Ser Asn
            355                 360                 365
Thr Thr Pro Glu Gly Val Ala Arg Arg Tyr Gly Gly Glu Trp Thr Glu
    370                 375                 380
Glu Ala Gly Glu Arg Ala Ala Leu Ser Glu Arg Leu Phe Ala Asn Leu
385                 390                 395                 400
Trp Gly Arg Leu Glu Gly Glu Arg Leu Leu Trp Leu Tyr Arg Glu
                405                 410                 415
Val Glu Arg Pro Leu Ser Ala Val Ala His Met Glu Ala Thr Gly
            420                 425                 430
Val Arg Leu Asp Val Ala Tyr Leu Arg Ala Leu Ser Leu Glu Val Ala
        435                 440                 445
Glu Glu Ile Ala Arg Leu Glu Ala Glu Val Phe Arg Leu Ala Gly His
    450                 455                 460
Pro Phe Asn Leu Asn Ser Arg Asp Gln Leu Glu Arg Val Leu Phe Asp
465                 470                 475                 480
Glu Leu Gly Leu Pro Ala Ile Gly Lys Thr Glu Lys Thr Gly Lys Arg
                485                 490                 495
Ser Thr Ser Ala Ala Val Leu Glu Ala Leu Arg Glu Ala His Pro Ile
            500                 505                 510
Val Glu Lys Ile Leu Gln Tyr Arg Glu Leu Thr Lys Leu Lys Ser Thr
        515                 520                 525
Tyr Ile Asp Pro Leu Pro Asp Leu Ile His Pro Arg Thr Gly Arg Leu
    530                 535                 540
His Thr Arg Phe Asn Gln Thr Ala Thr Ala Thr Gly Arg Leu Ser Ser
545                 550                 555                 560
Ser Asp Pro Asn Leu Gln Asn Ile Pro Val Arg Thr Pro Leu Gly Gln
                565                 570                 575
Arg Ile Arg Arg Ala Phe Ile Ala Glu Gly Trp Leu Leu Val Ala
            580                 585                 590
Leu Asp Tyr Ser Gln Ile Glu Leu Arg Val Leu Ala His Leu Ser Gly
        595                 600                 605
Asp Glu Asn Leu Ile Arg Val Phe Gln Glu Gly Arg Asp Ile His Thr
    610                 615                 620
Glu Thr Ala Ser Trp Met Phe Gly Val Pro Arg Glu Ala Val Asp Pro
625                 630                 635                 640
Leu Met Arg Arg Ala Ala Lys Thr Ile Asn Phe Gly Val Leu Tyr Gly
                645                 650                 655
Met Ser Ala His Arg Leu Ser Gln Glu Leu Ala Ile Pro Tyr Glu Glu
            660                 665                 670
Ala Gln Ala Phe Ile Glu Arg Tyr Phe Gln Ser Phe Pro Lys Val Arg
        675                 680                 685
Ala Trp Ile Glu Lys Thr Leu Glu Glu Gly Arg Arg Gly Tyr Val
    690                 695                 700
Glu Thr Leu Phe Gly Arg Arg Arg Tyr Val Pro Asn Leu Glu Ala Arg
705                 710                 715                 720
Val Lys Ser Val Arg Glu Ala Ala Glu Arg Met Ala Phe Asn Met Pro
                725                 730                 735
Val Gln Gly Thr Ala Ala Asp Leu Met Lys Leu Ala Met Val Lys Leu
            740                 745                 750
Phe Pro Arg Leu Glu Glu Met Gly Ala Arg Met Leu Leu Gln Val His
        755                 760                 765
Asp Glu Leu Val Leu Glu Ala Pro Lys Glu Arg Ala Glu Ala Val Ala
```

```
                770               775               780
Arg Leu Ala Lys Glu Val Met Glu Gly Val Tyr Pro Leu Ala Val Pro
785               790               795               800

Leu Glu Val Glu Val Gly Ile Gly Glu Asp Trp Leu Ser Ala Lys Glu
                805               810               815

<210> SEQ ID NO 14
<211> LENGTH: 554
<212> TYPE: PRT
<213> ORGANISM: Thermus aquaticus

<400> SEQUENCE: 14

Met Gly Leu Leu His Glu Phe Gly Leu Leu Glu Ser Pro Lys Ala Leu
1               5                   10                  15

Glu Glu Ala Pro Trp Pro Pro Glu Gly Ala Phe Val Gly Phe Val
                20                  25                  30

Leu Ser Arg Lys Glu Pro Met Trp Ala Asp Leu Leu Ala Leu Ala Ala
            35                  40                  45

Ala Arg Gly Gly Arg Val His Arg Ala Pro Glu Pro Tyr Lys Ala Leu
        50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
130                 135                 140

Glu Glu Arg Leu Leu Trp Leu Tyr Arg Glu Val Glu Arg Pro Leu Ser
145                 150                 155                 160

Ala Val Leu Ala His Met Glu Ala Thr Gly Val Arg Leu Asp Leu Ser
                165                 170                 175

Tyr Leu Arg Ala Leu Ser Leu Glu Val Ala Glu Glu Ile Ala Arg Leu
            180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Glu Leu Gly Leu Pro Ala
210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Met Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335
```

```
Glu Leu Arg Val Leu Ala His Leu Ser Gly Asp Glu Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
        370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
            420                 425                 430

Leu Glu Glu Gly Arg Arg Arg Gly Tyr Val Glu Thr Leu Phe Gly Arg
        435                 440                 445

Arg Arg Tyr Val Pro Asp Leu Glu Ala Arg Val Arg Ser Val Arg Glu
        450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
            515                 520                 525

Met Glu Gly Val Tyr Pro Leu Ala Val Pro Leu Glu Val Glu Val Gly
        530                 535                 540

Ile Gly Glu Asp Trp Leu Ser Ala Lys Glu
545                 550
```

INHIBITION-RESISTANT POLYMERASES

CROSS-REFERENCE TO RELATED APPLICATIONS

This application claims priority from U.S. Provisional Application Ser. No. 61/714,671, filed on 16 Oct. 2012, and U.S. Provisional Application Ser. No. 61/811,611, filed on 12 Apr. 2013, each of which is incorporated herein by reference in its entirety.

STATEMENT REGARDING FEDERALLY SPONSORED RESEARCH OR DEVELOPMENT

This invention was made with government support under grant number IIP1127479 awarded by National Science Foundation. The government has certain rights in the invention.

MATERIAL INCORPORATED-BY-REFERENCE

The Sequence Listing, which is a part of the present disclosure, includes a computer readable form comprising nucleotide or amino acid sequences of the present invention. The subject matter of the Sequence Listing is incorporated herein by reference in its entirety.

BACKGROUND OF THE INVENTION

Known mutant polymerases include Omni Taq, i.e., FL-22 (SEQ ID NO: 3) (as described in U.S. Patent Application Publication No. 2011/0027832) and Omni Klentaq, i.e., KlenTaq-10 (SEQ ID NO: 4) (as described in U.S. Patent Application Publication No. 2006/0084074).

Known mutant polymerases and uses thereof are described in, for example, U.S. Pat. No. 7,462,475, issued 9 Dec. 2008; U.S. Patent Application Publication No. 2009/0170060, published 2 Jul. 2009; U.S. Patent Application Publication No. 2011/0027832, published 3 Feb. 2011; U.S. Patent Application Publication No. 2012/0028259, published 2 Feb. 2012; and international PCT application WO2012/088479, published 28 Jun. 2012.

SUMMARY OF THE INVENTION

One aspect of the present disclosure includes an isolated mutant polypeptide having polymerase activity. In some embodiments, the isolated polypeptide includes an amino acid sequence at least 95% identical to SEQ ID NO: 1 having at least one amino acid substitution selected from the group consisting E404G, G418E, V453L, A454S, R487G, I528ML533R, D551G, D578E, I599V, L657Q, D732N, K738R, L781I, and E818V, or a functional fragment thereof, wherein the isolated polypeptide has polymerase activity.

In some embodiments, the functional fragment includes SEQ ID NO: 2 having at least one amino acid substitution selected from the group consisting of E404G, G418E, V453L, A454S, R487G, I528ML533R, D551G, D578E, I599V, L657Q, D732N, K738R, L781I, and E818V (per wild-type Taq numbering) and the functional fragment retains polymerase activity.

In some embodiments, the isolated polypeptide further includes at least one amino acid substitution selected from the group consisting of L609P, E626K, V649I, I707L, E708K, E708L, E708N, E708Q, E708I, E708W, E708R, E708V, or E708S (per wild-type Taq numbering).

In some embodiments, the isolated polypeptide has polymerase activity in the presence of an inhibitory substance in an amount sufficient to cause a wild type polymerase to fail to amplify a target nucleic acid in a polymerase chain reaction (PCR). In some embodiments, the isolated polypeptide has polymerase activity in the presence of an inhibitory substance in an amount sufficient to cause a wild type Taq polymerase of SEQ ID NO: 1 to fail to amplify a target nucleic acid in a polymerase chain reaction (PCR). In some embodiments, the inhibitory substance is contained in a sample of one or more of chocolate, peanut buffer, milk, seafood, meat, egg, plant material, blood, a blood fraction, urine, dye, soil, soil extract, humic acid, guanidinium thiocyanate (GITC), or ethanol.

In some embodiments, the isolated polypeptide is one of SEQ ID NO: 5 (mutant B-9), SEQ ID NO: 6 (mutant H-10), SEQ ID NO: 7 (mutant F-12), SEQ ID NO: 8 (mutant E-12), SEQ ID NO: 9 (mutant C-6), SEQ ID NO: 10 (mutant C-12), SEQ ID NO: 11 (mutant C-66), SEQ ID NO: 12 (mutant H-2), or SEQ ID NO: 13 (mutant A-111).

In some embodiments, the isolated polypeptide includes SEQ ID NO: 5 (mutant B-9) or a polypeptide sequence at least 95% identical to SEQ ID NO: 5 having 209G and polymerase activity.

In some embodiments, the isolated polypeptide includes SEQ ID NO: 6 (mutant H-10) or a polypeptide sequence at least 95% identical to SEQ ID NO: 6 having 140E and polymerase activity.

In some embodiments, the isolated polypeptide includes SEQ ID NO: 7 (mutant F-12) or a polypeptide sequence at least 95% identical to SEQ ID NO: 7 having 255R and polymerase activity.

In some embodiments, the isolated polypeptide includes SEQ ID NO: 8 (mutant E-12) or a polypeptide sequence at least 95% identical to SEQ ID NO: 8 having 503I and polymerase activity.

In some embodiments, the isolated polypeptide includes SEQ ID NO: 9 (mutant C-6) or a polypeptide sequence at least 95% identical to SEQ ID NO: 9 having 578E and polymerase activity.

In some embodiments, the isolated polypeptide includes SEQ ID NO: 10 (mutant C-12) or a polypeptide sequence at least 95% identical to SEQ ID NO: 10 having one or more of 551G, 599V, and 657Q and polymerase activity.

In some embodiments, the isolated polypeptide includes SEQ ID NO:11 (mutant C-66) or a polypeptide sequence at least 95% identical to SEQ ID NO: 11 having 818V and polymerase activity.

In some embodiments, the isolated polypeptide includes SEQ ID NO: 12 (mutant H-2) or a polypeptide sequence at least 95% identical to SEQ ID NO: 12 having 404G and polymerase activity.

In some embodiments, the isolated polypeptide includes SEQ ID NO: 13 (mutant A-111) or a polypeptide sequence at least 95% identical to SEQ ID NO: 13 having 732N and polymerase activity.

In some embodiments, the isolated polypeptide includes SEQ ID NO:14 (mutant H-101) or a polypeptide sequence at least 95% identical to SEQ ID NO:14 having one or more of 175L, 176S, 250M, or 460R and polymerase activity.

Another aspect of the present disclosure provides a method of amplifying a target nucleic acid in a polymerase chain reaction (PCR). In some embodiments, the method includes forming an assay mixture of a sample containing a target nucleic acid, primers specific for the target nucleic acid, a buffer, and an isolated polypeptide having polymerase activity described herein; and amplifying the target nucleic acid in the assay mixture in a PCR.

In some embodiments of the method, the sample includes an inhibitory substance in an amount sufficient to cause a wild type Taq polymerase (e.g., a polymerase of SEQ ID NO: 1) to fail to amplify the target nucleic acid in the PCR.

In some embodiments of the method, the inhibitory substance is present in the sample comprising one or more of chocolate, peanut buffer, milk, seafood, meat, egg, plant material, blood, a blood fraction, urine, dye, soil, soil extract, humic acid, guanidinium thiocyanate (GITC), or ethanol.

In some embodiments of the method, the assay mixture includes a dye up to about 100×, where X is a manufacturer unit for concentration for use in PCR. In some embodiments of the method, the assay mixture includes blood or a blood fraction up to about 40% of a total volume of the assay mixture. In some embodiments of the method, the assay mixture includes soil or soil extract up to about 50% of a total volume of the assay mixture or an equivalent amount that provides up to about 5 ng of humic acid per uL of the assay mixture volume. In some embodiments of the method, the assay mixture includes a bile salt, or an equivalent amount of bile, up to about 2 µg per µL of the assay mixture or up to about 20% of a total volume of the assay mixture. In some embodiments of the method, the assay mixture includes a plant material or a plant extract up to about 50% of a total volume of the assay mixture. In some embodiments of the method, the assay mixture includes urine up to about 90% of a total volume of the assay mixture. In some embodiments of the method, the assay mixture includes GITC up to about 200 mM in the assay mixture. In some embodiments of the method, the assay mixture includes ethanol up to about 10% of a total volume of the assay mixture. In some embodiments of the method, the assay mixture includes tea polyphenols up to about 12 ng per µl of assay mixture. In some embodiments of the method, the assay mixture includes tannins up to about 0.5 ug per µL of assay mixture. In some embodiments of the method, the assay mixture includes chocolate up to about 20 µg per µL of assay mixture. In some embodiments of the method, the assay mixture includes black pepper in an amount of up to 20 ug/ul of assay mixture.

In some embodiments of the method, the PCR is a real-time PCR; the assay mixture further comprises at least one dye; and amplifying the target nucleic acid comprises amplifying the target nucleic acid in the assay mixture in a real-time PCR.

Another aspect of the present disclosure provides a nucleic acid encoding an isolated polypeptide having polymerase activity described herein. In some embodiments, a DNA construct contains operably linked components of a promoter functional in a host cell, a transcribable nucleic acid molecule encoding an isolated polypeptide having polymerase activity described herein, and a 3' transcription termination sequence. In some embodiments is provided a host cell transformed with such a DNA construct, where the host cell expresses the encoded polymerase.

Another aspect of the present disclosure provides kit that includes the isolated polypeptide having polymerase activity described herein, or a nucleic acid encoding such, along with optional components useful or necessary for carrying out PCR or expressing a polymerase from a host cell.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
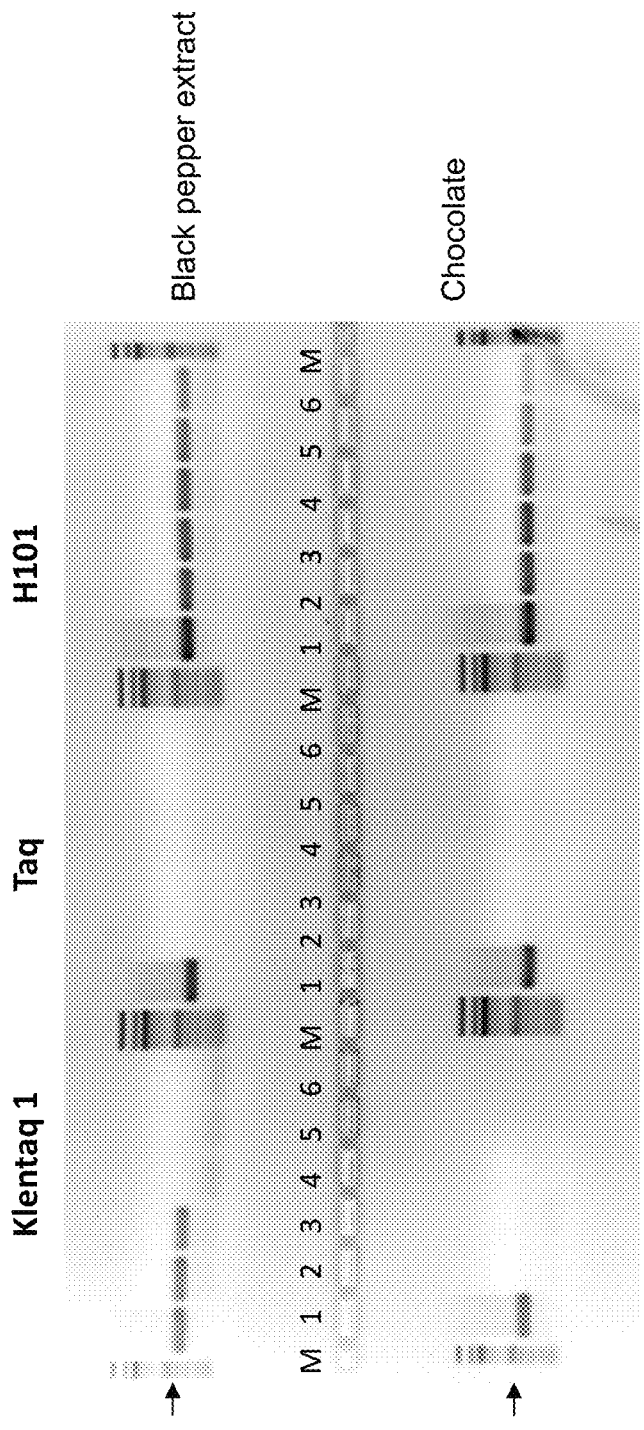
FIG. 1 is an image of a series of gels showing performance of H101 (SEQ ID NO: 14) Klentaq mutant with crude samples containing chocolate or black pepper. A 380 bp rRNA target was amplified from 1 ng bacterial DNA in 50 µl reactions with 15 U Klentaq 1, w.t. Taq (New England Biolabs), and the Klentaq1 mutant H101 (SEQ ID NO: 14) in the presence of 0, 3, 4, 5, 6 and 9 µl of a crude black pepper extract (50 mg/ml, top panel), or 0, 2, 2.5, 3.0, 3.5 and 4.5 µl 10% chocolate suspension (bottom panel), lanes 1-6. Lanes M, DNA ladder. The amplified products were analyzed in ethidium bromide stained agarose gel. Further details regarding methodology are available in Example 1.

The present disclosure is based at least in part on newly discovered Taq and Klentaq polymerase mutants that can tolerate high levels of major PCR inhibitors. In various embodiments, mutant DNA polymerase enzymes are resistant to PCR inhibitors including those present in, for example, food or food samples, such as chocolate, peanut butter, milk, seafood, meat, or egg, as well as blood, blood components, urine, humic acid, bile salts, plant tissue extracts, GITC (guanidinium) or ethanol. Such mutants and related compositions can replace key PCR components of enzyme, buffer and additives in commercially available kits, rendering them more robust and sensitive even in the presence of some PCR inhibitors, which usually can compromise detection. Also, mutant polymerases described herein can be used directly, without requiring a commercial kit. Provided herein are compositions and methods for end-point or real-time PCR analyses of samples containing inhibitory substances, such as food-containing samples, utilizing mutant polymerase enzymes that are inhibition resistant.

The following U.S. patent applications are incorporated herein by reference in their entirety: U.S. Pat. No. 7,462,475, issued 9 Dec. 2008; U.S. Patent Application Publication No. 2009/0170060, published 2 Jul. 2009; U.S. Patent Application Publication No. 2011/0027832, published 3 Feb. 2011; U.S. Patent Application Publication No. 2012/0028259, published 2 Feb. 2012; and international PCT application WO2012/088479, published 28 Jun. 2012. Except as otherwise noted herein, therefore, the process of the present disclosure can be carried out in accordance with compositions or processes of these references.

Mutant Polymerases

Some embodiments provide mutant polymerases that can be resistant to various PCR inhibitors.

According to conventional notation, amino acid mutations discussed herein may be represented, from left to right, by the one letter code for the wild type amino acid, the amino acid position number, and the one letter code for the mutant amino acid. For mutant polypeptide sequences, an amino acid different than corresponding wild type may be represented, from left to right, by the amino acid position number and the one letter code for the amino acid that is different than corresponding wild type.

A "variant" polypeptide described in the following paragraphs is as defined in the "variant" section further below. Exemplary sequence identity (e.g., at least about 95% sequence identity) is not meant to limit the full range of sequence identity as discussed in the "variant" section herein.

For the following discussion, wild type Taq numbering (corresponding to numbering of full-length Taq of SEQ ID NO: 1) is used in this descriptive text so as to make clear the relationship between the polypeptides. Wild type Taq (SEQ ID NO: 1) and truncated Klentaq-1 (SEQ ID NO: 2) have complete sequence homology across positions 279-832 of SEQ ID NO: 1, except for positions 279 (Gly) and 280 (Ser) of SEQ ID NO: 1 (corresponding to positions 1 (Met) and 2 (Gly) of truncated SEQ ID NO: 2). The amino acid changes at 279-280 of wild type Taq (SEQ ID NO: 1) and positions 1-2 of truncated Klentaq-1 (SEQ ID NO: 2) are not necessarily associated with a difference in phenotype as described herein.

With respect to wild-type Taq numbering, for truncated polymerase polypeptides (e.g., Klentaq-1 of SEQ ID NO: 2), position number 1 as notated in the Sequence Listing of SEQ ID NO: 2 corresponds to position number 279 as notated in the full-length Taq of SEQ ID NO: 1. Similarly, position number 2 of SEQ ID NO: 2 corresponds to position number 280 of SEQ ID NO: 1. Similarly, position number 554 of SEQ ID NO: 2 corresponds to position number 832 of SEQ ID NO: 1. In other words, one can determine the corresponding position in full-length SEQ ID NO: 1 by adding 278 the any position in SEQ ID NO: 2.

A mutant polymerase described herein can be produced according to methods known in the art. For example, oligonucleotides providing the specific amino acid changes to a mutant polymerase described can be prepared by standard synthetic techniques (e.g., an automated DNA synthesizer) and used as PCR primers in site-directed mutagenesis. Standard procedures of expression of mutant polymerase polypeptides from encoding DNA sequences can then be performed. Alternatively, the mutant DNA polymerase polypeptides can be directly synthesized according to methods known in the art.

A mutant polymerase having a mutation described herein can be a full length mutant polymerase or a truncated mutant polymerase, as compared to a wild-type Taq polymerase. For example, a truncated mutant polymerase can be truncated at position 278 per wild-type Taq numbering (e.g., position 1 of the truncated mutant corresponds to position 279 of SEQ ID NO: 1). One of skill in the art will understand that a truncated mutant polymerase can be truncated at any position of a full length sequence so long as polymerase activity is retained.

A truncated mutant polymerase can be referred to as a "functional fragment" of a longer polymerase, such as a full-length polymerase. For example, SEQ ID NO: 2 (Klentaq-1, KT-1) is a variant (having G279M and S280G per wild type Taq numbering) and functional fragment of SEQ ID NO: 1 (wild type Taq). As another example SEQ ID NO: 4 (Omni Kt, KT-10) is a functional fragment of SEQ ID NO: 3 (Omni Taq, FL-12). A functional fragment is shorter than the length of a reference polymerase and retains polymerase activity.

As disclosed herein, one or more amino acid mutations (e.g., addition, deletion, substitution) can be associated with a phenotype described herein. In some embodiments, a mutant polymerase (e.g., a full length mutant polymerase or a truncated mutant polymerase) can include one or more of the following substitutions: E404G, G418E, V453L, A454S, R487G, I528ML533R, D551G, D578E, I599V, L657Q, D732N, K738R, L781I, and E818V.

For example, a mutant polymerase can include SEQ ID NO: 1 having one or more substitutions selected from E404G, G418E, V453L, A454S, R487G, I528ML533R, D551G, D578E, I599V, L657Q, D732N, K738R, L781I, and E818V, or a variant (e.g., at least about 95% sequence identity) thereof having at least one of these substitutions and having polymerase activity.

As another example, a mutant polymerase can include SEQ ID NO: 2 having one or more substitutions selected from E404G, G418E, V453L, A454S, R487G, I528ML533R, D551G, D578E, I599V, L657Q, D732N, K738R, L781I, and E818V (per wild-type Taq numbering), or a variant (e.g., at least about 95% sequence identity) thereof having at least one of these substitutions and having polymerase activity.

In some embodiments, a mutant polymerase (e.g., a full length mutant polymerase or a truncated mutant polymerase) can include one or more of the following substitutions: L609P, E626K, V649I, I707L, E708K, E708L, E708N, E708Q, E708I, E708W, E708R, E708V, or E708S (per wild type numbering). A substitution at one or more of these positions (e.g., 708) can occur in combination with one or more other substitutions described herein. For example, a mutant polymerase (e.g., a full length mutant polymerase or a truncated mutant polymerase) can have (a) at least one substitution selected from E404G, G418E, V453L, A454S, R487G, I528ML533R, D551G, D578E, I599V, L657Q, D732N, K738R, L781I, and E818V and (b) at least one substitution selected from L609P, E626K, V649I, I707L, E708K, E708L, E708N, E708Q, E708I, E708W, E708R, E708V, and E708S (per wild type numbering). As another example, a mutant polymerase can include SEQ ID NO: 1 having (a) at least one substitution selected from E404G, G418E, V453L, A454S, R487G, I528ML533R, D551G, D578E, I599V, L657Q, D732N, K738R, L781I, and E818V and (b) at least one substitution selected from L609P, E626K, V649I, I707L, E708K, E708L, E708N, E708Q, E708I, E708W, E708R, E708V, and E708S (per wild type numbering). As another example, a mutant polymerase can include SEQ ID NO: 2 having (a) at least one substitution selected from E404G, G418E, V453L, A454S, R487G, I528ML533R, D551G, D578E, I599V, L657Q, D732N, K738R, L781I, and E818V (per wild-type Taq numbering) and (b) at least one substitution selected from L609P, E626K, V649I, I707L, E708K, E708L, E708N, E708Q, E708I, E708W, E708R, E708V, and E708S (per wild-type Taq numbering).

In some embodiments, a mutant polymerase (e.g., a full length or truncated mutant polymerase) can include one or more of the following substitutions: E626K, I707L, E708K, R487G, V453L, A454S, I528M, L533M, and K738R (per wild type Taq numbering). As another example, a mutant polymerase (e.g., a full length or truncated mutant polymerase) can include one or more of the following substitutions: R487G, V453L, A454S, I528M, L533M, and K738R. B-9.

A mutant polymerase can include an amino acid sequence of SEQ ID NO: 5 (mutant B-9), or a variant (e.g., at least about 95% sequence identity) thereof having 209G and retaining polymerase activity. Note that 209G in SEQ ID NO: 5 corresponds to R487G according to wild type Taq numbering.

A mutant polymerase can include an amino acid sequence of SEQ ID NO: 2 having mutation R209G, or a variant (e.g., at least about 95% sequence identity) thereof with R209G and retaining polymerase activity. Note that R209G in SEQ ID NO: 2 corresponds to R487G according to wild type Taq numbering.

A mutant polymerase can include an amino acid sequence of positions 279-832 of SEQ ID NO: 1 having mutation R487G (according to wild-type Taq numbering), or a variant (e.g., at least about 95% sequence identity) thereof with R487G and retaining polymerase activity.

H-10.

A mutant polymerase can include an amino acid sequence of SEQ ID NO: 6 (mutant H-10), or a variant (e.g., at least about 95% sequence identity) thereof having 140E and retaining polymerase activity. Note that 140E in SEQ ID NO: 6 corresponds to G418E according to wild type Taq numbering. For example, a mutant polymerase can be a variant (e.g., at least about 95% sequence identity) of an amino acid sequence of SEQ ID NO: 6 having one or more of 140E, 348K, 429L, or 430S and retaining polymerase activity. Note that 348K, 429L, and 430S in SEQ ID NO: 6 correspond to E626K, I707L, and E708S according to wild type Taq numbering.

A mutant polymerase can include an amino acid sequence of SEQ ID NO: 2 having mutation G140E, or a variant (e.g., at least about 95% sequence identity) thereof with G140E and retaining polymerase activity. Note that G140E in SEQ ID NO: 2 corresponds to G418E according to wild type Taq numbering. For example, a mutant polymerase can be a variant (e.g., at least about 95% sequence identity) of an amino acid sequence of SEQ ID NO: 2 having one or more of G140E, E348K, I429L, or E430S and retaining polymerase activity.

A mutant polymerase can include an amino acid sequence of positions 279-832 of SEQ ID NO: 1 having mutation G418E (according to wild-type Taq numbering), or a variant (e.g., at least about 95% sequence identity) thereof with G418E and retaining polymerase activity. For example, a mutant polymerase can be a variant (e.g., at least about 95% sequence identity) of an amino acid sequence of SEQ ID NO: 1 having one or more of G418E, E626K, I707L, and E708S and retaining polymerase activity.

F-12.

A mutant polymerase can include an amino acid sequence of SEQ ID NO: 7 (mutant F-12), or a variant (e.g., at least about 95% sequence identity) thereof having 255R and retaining polymerase activity. Note that 255R in SEQ ID NO: 7 corresponds to L533R according to wild type Taq numbering.

A mutant polymerase can include an amino acid sequence of SEQ ID NO: 2 having mutation L255R, or a variant (e.g., at least about 95% sequence identity) thereof with L255R and retaining polymerase activity. Note that L255R in SEQ ID NO: 2 corresponds to L533R according to wild type Taq numbering.

A mutant polymerase can include an amino acid sequence of positions 279-832 of SEQ ID NO: 1 having mutation L533R (according to wild-type Taq numbering), or a variant (e.g., at least about 95% sequence identity) thereof with L533R and retaining polymerase activity.

E-12.

A mutant polymerase can include an amino acid sequence of SEQ ID NO: 8 (mutant E-12), or a variant (e.g., at least about 95% sequence identity) thereof having 503I and retaining polymerase activity. Note that 503I in SEQ ID NO: 8 corresponds to L781I according to wild type Taq numbering.

A mutant polymerase can include an amino acid sequence of SEQ ID NO: 2 having mutation L503I, or a variant (e.g., at least about 95% sequence identity) thereof with L503I and retaining polymerase activity. Note that L503I in SEQ ID NO: 2 corresponds to L781I according to wild type Taq numbering.

A mutant polymerase can include an amino acid sequence of positions 279-832 of SEQ ID NO: 1 having mutation L781I (according to wild-type Taq numbering), or a variant (e.g., at least about 95% sequence identity) thereof with L781I and retaining polymerase activity.

H-101.

A mutant polymerase can include an amino acid sequence of SEQ ID NO: 14 (mutant H-101), or a variant (e.g., at least about 95% sequence identity) thereof having at least one of 175L, 176S, 250M, or 460R and retaining polymerase activity. Note that 175L, 176S, 250M, and 460R in SEQ ID NO: 14 corresponds to V453L, A454S, I528M, and K738R, respectively, according to wild type Taq numbering.

A mutant polymerase can include an amino acid sequence of SEQ ID NO: 2 having mutations V175L, A176S, I250M, and K460R, or a variant (e.g., at least about 95% sequence identity) thereof with at least one of V175L, A176S, I250M, or K460R and retaining polymerase activity. Note that V175L, A176S, I250M, and K460R in SEQ ID NO: 2 corresponds to V453L, A454S, I528M, and K738R, respectively, according to wild type Taq numbering.

A mutant polymerase can include an amino acid sequence of positions 279-832 of SEQ ID NO: 1 having mutation V453L, A454S, I528M, and K738R (according to wild-type Taq numbering), or a variant (e.g., at least about 95% sequence identity) thereof with at least one of V453L, A454S, I528M, and K738R and retaining polymerase activity.

C-6.

A mutant polymerase can include an amino acid sequence of SEQ ID NO: 9 (mutant C-6), or a variant (e.g., at least about 95% sequence identity) thereof having 578E and retaining polymerase activity. Note that 578E in SEQ ID NO: 9 corresponds to D578E according to wild type Taq numbering.

A mutant polymerase can include an amino acid sequence of SEQ ID NO: 1 having mutation D578E (according to wild-type Taq numbering), or a variant (e.g., at least about 95% sequence identity) thereof with D578E and retaining polymerase activity.

C-12.

A mutant polymerase can include an amino acid sequence of SEQ ID NO: 10 (mutant C-12), or a variant (e.g., at least about 95% sequence identity) thereof having 551G, 599V, and 657Q and retaining polymerase activity. Note that 551G, 599V, and 657Q in SEQ ID NO: 10 correspond to D551G, I599V, and L657Q, respectively, according to wild type Taq numbering.

A mutant polymerase can include an amino acid sequence of SEQ ID NO: 1 having one or more mutations of D551G, I599V, and L657Q (according to wild-type Taq numbering), or a variant (e.g., at least about 95% sequence identity) thereof with one or more mutations of D551G, I599V, and L657Q and retaining polymerase activity.

C-66.

A mutant polymerase can include an amino acid sequence of SEQ ID NO: 11 (mutant C-66), or a variant (e.g., at least about 95% sequence identity) thereof having 818V and retaining polymerase activity. Note that 818V in SEQ ID NO: 11 corresponds to E818V according to wild type Taq numbering.

A mutant polymerase can include an amino acid sequence of SEQ ID NO: 1 having mutation E818V (according to wild-type Taq numbering), or a variant (e.g., at least about 95% sequence identity) thereof with E818V and retaining polymerase activity.

H-2.

A mutant polymerase can include an amino acid sequence of SEQ ID NO: 12 (mutant H-2), or a variant (e.g., at least about 95% sequence identity) thereof having 404G and retaining polymerase activity. Note that 404G in SEQ ID NO: 12 corresponds to E404G according to wild type Taq numbering.

A mutant polymerase can include an amino acid sequence of SEQ ID NO: 1 having mutation E404G (according to wild-type Taq numbering), or a variant (e.g., at least about 95% sequence identity) thereof with E404G and retaining polymerase activity.

A-111.

A mutant polymerase can include an amino acid sequence of SEQ ID NO: 13 (mutant A-111), or a variant (e.g., at least about 95% sequence identity) thereof having 732N and retaining polymerase activity. Note that 732N in SEQ ID NO: 13 corresponds to D732N according to wild type Taq numbering.

A mutant polymerase can include an amino acid sequence of SEQ ID NO: 1 having mutation D732N (according to wild-type Taq numbering), or a variant (e.g., at least about 95% sequence identity) thereof with D732N and retaining polymerase activity.

A mutant polymerase described herein can be used in conjunction with compositions or processes described in U.S. Pat. Nos. 6,403,341; 7,393,635; 7,462,475; WO 2012/088479 (and corresponding U.S. application Ser. No. 13/997,194); and US Pat App Pub No. 2012/0028259, each incorporated herein by reference.

Another aspect of the present disclosure provides a polynucleotide encoding a mutant polymerase described herein. Also provided is a nucleic acid construct (e.g., an expression vector) including polynucleotide encoding a mutant polymerase described herein. A construct (e.g., a DNA construct) can include the following operably associated components: a promoter functional in a host cell, a nucleotide sequence (e.g., a heterologous DNA sequence, an exogenous DNA segment, or a heterologous nucleic acid) encoding a mutant polymerase described herein, a transcriptional termination sequence. Generation of an encoding polynucleotide, a nucleic acid construct (e.g., an expression vector), transformation of a host cell with such construct, and expression of a mutant polymerase from a transformed host cell is within the state of the art.

Variants

The term "variant" polypeptides (or encoding polynucleotides) is discussed below. The description of "variant" below is incorporated by reference into each recitation of "variant" in the description of mutant polymerases herein. For example, the full range of sequence identity discussed below applies equally to "variant" polypeptides discussed elsewhere herein.

Included in the scope of the present disclosure are variant polypeptides (or encoding polynucleotides) with at least 80% sequence identity to sequences described herein, so long as such variants retain a polymerase activity (e.g., a resistant polymerase activity).

For example, a variant polypeptide (or an encoding polynucleotide) with polymerase activity can have at least about 85%, 86%, 87%, 88%, 89%, 90%, 91%, 92%, 93%, 94%, 95%, 96%, 97%, 98%, 99%, or 99.9% sequence identity to sequences disclosed herein (including disclosed sequences having substitutions described herein). It is understood that in some embodiments, "about" modifies each of these recited sequence identity values. A variant polypeptide (or encoding polynucleotides) with polymerase activity can have at least 95% sequence identity to a sequence disclosed herein. A variant polypeptide (or an encoding polynucleotide) with polymerase activity can have at least 99% sequence identity to a sequence disclosed herein. The species are representative of the genus of variant polypeptides of each of these respective sequences because all variants must possess the specified catalytic activity (e.g., resistant polymerase activity) and must have the percent identity required above to the reference sequence.

Design, generation, and testing of the variant polypeptides having the above required percent identities to the sequences of the mutant DNA polymerases and retaining a required resistant phenotype is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of polypeptide variants having, for example, at least 95-99% identity to the sequences of mutant DNA polymerases described herein and screen such for phenotypes including, dye-resistance, blood-resistance, or soil-resistance according to methods routine in the art. Generally, conservative substitutions can be made at any position so long as the required activity is retained.

Amino acid sequence identity percent (%) is understood as the percentage of amino acid residues that are identical with amino acid residues in a candidate sequence in comparison to a reference sequence when the two sequences are aligned. To determine percent amino acid identity, sequences are aligned and if necessary, gaps are introduced to achieve the maximum percent sequence identity; conservative substitutions are not considered as part of the sequence identity. Amino acid sequence alignment procedures to determine percent identity are well known to those of skill in the art. Often publicly available computer software, such as BLAST, BLAST2, ALIGN2 or Megalign (DNASTAR) software, is used to align peptide sequences. Those skilled in the art can determine appropriate parameters for measuring alignment, including any algorithms needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B, and Y is the total number of amino acid residues in B. If the length of amino acid sequence A is not equal to the length of amino acid sequence B, the percent amino acid sequence identity of A to B will not equal the percent amino acid sequence identity of B to A.

Phenotype

As described herein, a mutant polymerase described herein can have polymerase activity and a resistance to one or more substances that can inhibit PCR. A mutant polymerase described herein can have a phenotype including polymerase activity and an ability to fully or partially complete a PCR in a reaction mixture including an inhibitory substance at a concentration that a wild type Taq polymerase (e.g., SEQ ID NO: 1) would fail to amplify a target nucleic acid. Resistant polymerase activity can be retention of all or most polymerase activity, or sufficient polymerase to complete a PCR, in the presence of a sample containing one or more of chocolate, pepper, milk, seafood, meat, egg, blood, urine, humic acid, bile, or plant material in sufficient quantity to inhibit or substantially inhibit a corresponding wild type polymerase.

A polymerase enzyme is understood to a add a free nucleotide to an —OH group on the 3' end of a newly forming nucleic acid strand, resulting in elongation of the strand in a 5'-3' direction. Directionality of the newly forming strand (the daughter strand) is understood to be opposite to the direction in which a polymerase moves along a template strand. Thus, a polymerase moves along the template strand in a 3'-5' direction, and the daughter strand is formed in a 5'-3' direction. In some embodiments, polymerase activity includes the ability of a polymerase to fully or partially complete a PCR. PCR is described further below.

A phenotype of a mutant polymerase described herein can have polymerase activity and resistance to one or more substances that can inhibit PCR. A mutant polymerase described herein can have a phenotype including polymerase activity and an ability to fully or partially complete a PCR in a reaction mixture including an inhibitory substance at a concentration that a wild type Taq polymerase would fail to amplify a target nucleic acid. An inhibitory substance can be present in food or food samples, such as chocolate, peanut butter, milk, seafood, meat, or egg, or other foods or food samples. GITC (guanidinium) or ethanol are exemplary of a target nucleic acid in a sample containing an inhibitory substance at a level inhibitory to a wild type Taq, Klentaq, Omni Taq, or Omni Klentaq.

Phenotypes of exemplary mutant polymerases are described in TABLE 1. Each amino acid change recited in Table 1 can occur independently or in combination with one or more other amino acid changes in a mutant polymerase of the present disclosure.

TABLE 1

Mutant Enzymes.

| Mutant | Length | AA Changes (w. t.#) | Choc. Resist. | Black Pepper Resist. | GITC* | EtOH | Blood Resist. | Humic Resist. | Bile Resist. | Plant# Resist. |
|---|---|---|---|---|---|---|---|---|---|---|
| Omni KT (SEQ ID NO: 4) | KT | E626K I707L E708K | + | + | Not tested | Not tested | + | ++ | + | + |
| B-9 (SEQ ID NO: 5) | KT | R487G | +++ | +++ | Not tested | Not tested | ++ | +++ | +++ | ++ |
| H-10 (SEQ ID NO: 6) | KT | G418E E626K I707L E708S | +++ | +++ | Not tested | Not tested | ++(+) | +++ | +++ | ++ |
| F-12 (SEQ ID NO: 7) | KT | L533R | ++ | ++ | Not tested | Not tested | +++ | ++ | ++ | Not tested |
| E-12 (SEQ ID NO: 8) | KT | L781I | ++ | +++ | Not tested | Not tested | ++ | ++ | +++ | Not tested |
| H-101 (SEQ ID NO: 14) | KT | V453L A454S I528M K738R | ++ | +++ | Not tested | Not tested | +++ | +++ | ++ | Not tested |
| Omni Taq (SEQ ID NO: 3) | Taq | E626K I707L E708N | + | + | Not tested | Not tested | + | + | + | + |
| C-6 (SEQ ID NO: 9) | Taq | D578E | +++ | ++ | +++ | +++ | Not tested | ++ | +++ | ++ |
| C-12 (SEQ ID NO: 10) | Taq | D551G, I599V, L657Q | +++ | +++ | Not tested | Not tested | Not tested | ++ | +++ | ++ |
| C-66 (SEQ ID NO: 11) | Taq | E818V | +++ | +++ | Not tested | Not tested | +++ | ++ | +++ | +++ |
| H-2 (SEQ ID NO: 12) | Taq | E404G | +++ | +++ | +++ | +++ | +++ | +++ | +++ | +++ |
| A-111 (SEQ ID NO: 13) | Taq | D732N | ++ | ++ | Not tested | Not tested | +++ | + | +++ | ++ |

Substitutions are according to wild-type Taq numbering.
Phenotype features: the performance of the enzymes in the presence of various PCR inhibitors is given in scale (+ to +++), relative to the Omni Klentaq (Klentaq-10) or OmniTaq (FL-22) mutants performance.
In the case of blood, +, ++, and +++ roughly correspond to functionality in 10%, 20%, and 40% blood, respectively.
*GITC stands for Guanidinium isothiocyanate.
Tobacco Leaf Extract used as challenging PCR inhibitor in the last column.

inhibitory substance that can be present in an assay mixture. An inhibitory substance can be present in chocolate, pepper, blood, urine, humic acid, bile, tannins, melanin, indigo dyes, or plant material. For example, an inhibitory substance can be a polyphenol, such as a polyphenol present in a sample described above. Thus, a mutant polymerase described herein can be used to amplify a target polynucleotide in a PCR in the presence of one or more inhibitory substances.

Generally, a mutant polymerase described herein can tolerate at least an order of magnitude greater concentration of an inhibitory substance described herein as compared to a conventional polymerase (e.g., wild-type Taq). A mutant polymerase described herein can provide for amplification Dyes.

Various embodiments of the mutant polymerase enzymes described herein can tolerate increased concentrations of dyes, such as those used in real-time PCR (qPCR). A mutant polymerase can be used to amplify a DNA target in a real-time PCR of a DNA target in the presence of an inhibitory dye. A mutant polymerase can be used in combination with an enzyme having reverse transcriptase activity to amplify an RNA target in a real-time reverse transcriptase (RT) PCR of an RNA target in the presence of an inhibitory dye. Such increased concentrations include, but are not limited to, up to about 0.5×, 1×, 1.5×, 2×, 2.5×, 3×, 3.5×, 4×, 4.5×, 5×, 5.5×, 6×, 6.5×, 7×, 7.5×, 8×, 8.5×, 9×, 9.5×, 10×, 15×, 20×, 25×, 30×, 35×, 40×, 45×, 50×, 55×, 60×, 65×, 70×, 80×, 90×, or 100×, or even higher over the dye concentration conventionally used in the assay. As an example, X can be the standard manufacturers unit for dye concentration provided in a commercial product (e.g., SYBR Green, Molecular Probes, Eugene, Oreg.). For example, for SYBR Green, X corresponds to a concentration of about 10 μM.

Dye-resistance can be readily determined by assays known in the art and described in US Pat App Pub No. 2011/0027832.

Dyes for use in the methods described herein include, but are not limited to, SYBR Green (Molecular Probes, Eugene, Oreg.), LC Green (Idaho Technology, Salt Lake City, Utah), PicoGreen (Molecular Probes, Eugene, Oreg.), TOTO (Molecular Probes, Eugene, Oreg.), YOYO (Molecular Probes, Eugene, Oreg.) and SYTO9 (Molecular Probes, Eugene, Oreg.).

A dye can be a nucleic acid intercalating dye. A nucleic acid intercalating dye is understood to be a molecule that bind to nucleic acids in a reversible, non-covalent fashion, by insertion between the base pairs of the double helix, thereby indicating the presence and amount of nucleic acids. Generally, nucleic acid intercalating dyes are planar, aromatic, ring-shaped chromophore molecules. In some embodiments, intercalating dyes include fluorescent dyes. Numerous intercalating dyes are known in the art. Some non-limiting examples include PICO GREEN (P-7581, Molecular Probes), EB (E-8751, Sigma), propidium iodide (P-4170, Sigma), Acridine orange (A-6014, Sigma), 7-aminoactinomycin D (A-1310, Molecular Probes), cyanine dyes (e.g., TOTO, YOYO, BOBO, and POPO), SYTO, SYBR Green I, SYBR Green II, SYBR DX, OliGreen, CyQuant GR, SYTOX Green, SYTO9, SYTOIO, SYTO 17, SYBRI 4, FUN-I, DEAD Red, Hexidium Iodide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, and LDS 751 (U.S. Pat. No. 6,210,885), BOXTO, LC Green, Evagreen, Bebo.

With their tolerance to high dye concentrations, the mutant polymerases described herein can outperform other conventional polymerase enzymes, including top commercial PCR enzymes, with commercially available dyes used in qPCR including, but not limited to, SYBR Green, LC Green (Idaho Technology, Salt Lake City, Utah), PICO, TOTO (Molecular Probes, Eugene, Oreg.), YOYO (Molecular Probes, Eugene, Oreg.), SYTO (Molecular Probes, Eugene, Oreg.), and ethidium bromide. Some of these dyes are even more inhibitory than SYBR Green to a conventional Taq enzyme in PCR.

Blood.

In some embodiments, a mutant polymerase described herein can amplify a target nucleic acid in the presence of blood or blood components. A mutant polymerase can be used to amplify a DNA target in a real-time PCR of a DNA target in the presence of blood or blood components. A mutant polymerase can be used in combination with an enzyme having reverse transcriptase activity to amplify an RNA target in a real-time reverse transcriptase (RT) PCR of an RNA target in the presence of blood or blood components.

Blood-resistance can be readily determined by assays described in US Pat App Pub No. 2006/0084074 or US Pat App Pub No. 2011/0027832.

Whole blood generally comprises plasma, serum, and blood cells. Blood components include, but are not limited to, red blood cells, white blood cells (e.g., leukocytes or platelets, i.e., thrombocytes), plasma, serum, hemoglobin, water, proteins, glucose, amino acids, fatty acids, mineral ions, hormones, carbon dioxide, urea, and lactic acid. A mutant polymerase described herein can be used in PCR to amplify a nucleic acid target in the presence of one or more such blood components.

Blood plasma is generally understood as a liquid suspension in which blood cells are circulated. Thus, blood plasma can include one or more of water, proteins, glucose, amino acids, fatty acids, mineral ions, hormones, carbon dioxide, urea, lactic acid, platelets (i.e., thrombocytes), and blood cells. In a human subject, blood plasma represents about 55% of whole blood, or about 2.7 to 3 liters in an average human subject. Blood plasma contains about 92% water, 8% blood plasma proteins, and trace amounts of other materials. Blood plasma can contain serum albumin, blood-clotting factors, immunoglobulins, lipoproteins, other proteins, and electrolytes (e.g., sodium and chloride). A crude sample comprising blood plasma can also contain blood cells. A mutant polymerase described herein can be used in PCR to amplify a nucleic acid target in the presence of blood plasma.

Blood serum is generally understood as plasma from which clotting proteins have been removed, leaving mostly albumin and immunoglobulins. A mutant polymerase described herein can be used in PCR to amplify a nucleic acid target in the presence of blood serum.

In some embodiments, a mutant polymerase can display amplification activity in PCR assays (e.g., end point or real-time PCR) containing from about 1% to about 40% whole blood in the reaction mixture (vol/vol). For example, whole blood can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% of a total volume of a PCR assay mixture comprising a mutant polymerase described herein. In contrast, the full-length wild-type Taq enzyme (SEQ ID NO: 1) is usually completely inhibited in a blood concentration range of about 0.004% to about 0.2% whole blood in the reaction mixture (vol/vol).

In some embodiments, a mutant polymerase can display amplification activity in PCR assays (e.g., end point or real-time PCR) containing from about 1% to about 25% blood plasma in the reaction mixture (vol/vol). For example, blood plasma can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a mutant polymerase described herein.

In some embodiments, a mutant polymerase can display amplification activity in PCR assays (e.g., end point or real-time PCR) containing from about 1% to about 25% blood serum in the reaction mixture (vol/vol). For example, blood serum can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of a total volume of a PCR assay mixture comprising a mutant polymerase described herein.

Soil.

In some embodiments, a mutant polymerase described herein can amplify a target nucleic acid in the presence of an inhibitor found in soil or soil extract. A mutant polymerase can be used to amplify a DNA target in a real-time PCR of a DNA target in the presence of an inhibitor found in soil or soil extract. A mutant polymerase can be used in combination with an enzyme having reverse transcriptase activity to amplify an RNA target in a real-time reverse transcriptase (RT) PCR of an RNA target in the presence of an inhibitor found in soil or soil extract.

Soil inhibitors and soil extract inhibitors include, but are not limited to, humic acid, fulvic acid, polysaccarides, and metal ions. A mutant polymerase can display amplification activity in PCR assays containing from about 1% to about 50% soil or soil extract in the reaction mixture (vol/vol). For example, soil extract can comprise up to about 50%, 45%, 40%, 35%, 30%, 25%, 20%, 15%, 10%, 5%, or 1% of a total volume of a PCR assay mixture comprising a mutant polymerase described herein. The amount of soil or soil extract in the assay mixture can depend upon the levels of inhibitory substances in the soil or soil extract. Generally, a mutant polymerase described herein can tolerate at least an order of magnitude greater concentration of these inhibitory substances, as compared to a conventional polymerase (e.g., wild-type Taq). Assays to determine the level of inhibitory substances in a sample are known in the art. Soil-resistance can be readily determined by assays described in US Pat App Pub No. 2011/0027832.

Direct extraction of total DNA from soil samples can result in a co-extraction of humic acid, known as the most potent soil inhibitor to PCR analysis. Humic substances represent a mixture of partially characterized polyphenols that are produced during the decomposition of organic matter. Conventional DNA polymerase enzymes are inhibited at about 1 ng of humic acid per 50 uL reaction volume. Various embodiments of the mutant polymerases described herein are resistant to soil or soil extract that contains, for example, various levels of humic acid. Preferably, the volume of soil or soil extract used in the PCR assay mixture is the soil or soil extract equivalent that provides up to about 200 ng of humic acid per 50 uL reaction volume. For example, the volume of soil or soil extract used in the PCR assay mixture can be the soil or soil extract equivalent that provides from about 1 ng up to about 200 ng of humic acid per 50 uL reaction volume. As another example, the volume of soil or soil extract used in the PCR assay mixture can be the soil or soil extract equivalent that provides from about 5 ng up to about 200 ng of humic acid per 50 uL reaction volume. As another example, the volume of soil or soil extract used in the PCR assay mixture can be the soil or soil extract equivalent that provides about 1 ng, about 5 ng, about 10 ng, about 20 ng, about 30 ng, about 40 ng, about 50 ng, about 60 ng, about 70 ng, about 75 ng, about 80 ng, about 85 ng, about 90 ng, about 95 ng, about 100 ng, about 110 ng, about 120 ng, about 130 ng, about 140 ng, about 140 ng, about 150 ng, about 160 ng, about 170 ng, about 180 ng, about 190 ng, or about 200 ng of humic acid per 50 uL reaction volume. Assays to determine the amount of humic acid is a sample are known in the art.

Bile.

In some embodiments, a mutant polymerase described herein can amplify a target nucleic acid in the presence of bile or bile salts, a known PCR inhibitor. A mutant polymerase can be used to amplify a DNA target in a real-time PCR of a DNA target in the presence of bile. A mutant polymerase can be used in combination with an enzyme having reverse transcriptase activity to amplify an RNA target in a real-time reverse transcriptase (RT) PCR of an RNA target in the presence of bile.

A mutant polymerase described herein can provide for amplification of a target nucleic acid in a sample containing bile or bile salts at a level inhibitory to a wild type Taq, Klentaq, Omni Taq, or Omni Klentaq. Bile is understood to contain about 10% bile salts. Values recited below for bile salt extract can be extrapolated to bile.

For example, bile salts (or an equivalent amount of bile) can comprise up to about 100 μg per 50 μL reaction volume comprising a mutant polymerase described herein. As another example, bile salt extract (or an equivalent amount of bile) can comprise about 1 μg, 10 μg, 20 μg, 30 μg, 40 μg, 50 μg, 60 μg, 70 μg, 80 μg, 90 μg, or 100 μg per 50 μL reaction volume comprising a mutant polymerase described herein.

For example, bile salt extract (or an equivalent amount of bile) can comprise from about 0.1% up to about 20% of a total volume of a PCR assay mixture comprising a mutant polymerase described herein. As another example, bile salt extract (or an equivalent amount of bile) can comprise about 1.6% up to about 4% of a total volume of a PCR assay mixture comprising a mutant polymerase described herein. As another example, bile salt extract (or an equivalent amount of bile) can comprise about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% or more of a total volume of a PCR assay mixture comprising a mutant polymerase described herein. As another example, bile salt extract (or an equivalent amount thereof) can comprise about 0.8%, 1.6%, 2.4%, 3.2%, or 4.0% (see e.g., Example 10, FIG. 10).

Bile can contain one or more of the following: cholic acid, chenodeoxycholic acid, glycocholic acid, taurocholic acid, deoxycholic acid, or lithocholic acid. A mutant polymerase described herein can provide for amplification of a target nucleic acid in a sample containing one or more of cholic acid, chenodeoxycholic acid, glycocholic acid, taurocholic acid, deoxycholic acid, or lithocholic acid at a level inhibitory to a wild type Taq, Klentaq, Omni Taq, or Omni Klentaq.

Generally, a mutant polymerase described herein can tolerate at least an order of magnitude greater concentration of these inhibitory substances, as compared to a conventional polymerase (e.g., wild-type Taq). A mutant polymerase described herein can provide for amplification of a target nucleic acid in a sample containing bile or bile salt extract at a level inhibitory to a wild type Taq, Klentaq, Omni Taq, or Omni Klentaq.

Plant.

In some embodiments, a mutant polymerase described herein can amplify a target nucleic acid in the presence of an inhibitor found in plant material or a plant extract. A mutant polymerase can be used to amplify a DNA target in a real-time PCR of a DNA target in the presence of an inhibitor found in plant material or a plant extract. A mutant polymerase can be used in combination with an enzyme having reverse transcriptase activity to amplify an RNA target in a real-time reverse transcriptase (RT) PCR of an RNA target in the presence of an inhibitor found in plant material or a plant extract.

Plant material or plant extract inhibitors include, but are not limited to, polyphenols or condensed tannins. A sample containing plant or plant extract can contain condensed tannins at up to about 50% of dry weight. Such a sample or fraction thereof can be included in an assay mixture. For example, plant material or plant extract can comprise at least about 1% up to about 50%; at least about 1% up to about 50%; at least about 1% up to about 40%; at least about 1% up to about 30%; at least about 1% up to about 20%; or at least about 1% up to about 10% of a total volume of a PCR assay mixture comprising a mutant polymerase described herein. For example, plant material or a plant extract can comprise up to about 50%, 45%, 40%, 35%, 30%, 25%, 20%, 15%, 10%, 5%, or 1% of a total volume of a PCR assay mixture comprising a mutant polymerase described herein. The amount of plant material or a plant extract in the assay mixture can depend upon the levels of inhibitory substances in the plant material or a plant extract. Generally, a mutant polymerase described herein can tolerate at least an order of magnitude greater concentration of these inhibitory substances, as compared to a conventional polymerase (e.g., wild-type Taq). Assays to determine the level of inhibitory substances in a sample are known in the art.

Exemplary plant material, or extract thereof, includes, but is not limited to, soybean, tomato, tobacco, or tea.

A mutant polymerase described herein can provide for amplification of a target nucleic acid in a sample containing up to about 300 ng of tea polyphenols per 25 µl reaction volume. For example, a mutant polymerase described herein can provide for amplification of a target nucleic acid in a sample containing up to about 50 ng, up to about 75 ng, up to about 100 ng, up to about 125 ng, up to about 150 ng, up to about 175 ng, up to about 200 ng, up to about 225 ng, up to about 250 ng, up to about 275 ng, or up to about 300 ng of tea polyphenols per 25 µl reaction volume.

As another example, an assay mixture containing a mutant polymerase described herein can contain plant or plant extract at an equivalent amount that provides up to about 25 ug of tannins per 50 µL reaction volume; up to about 20 ug of tannins per 50 µL reaction volume; or up to about 10 ug of tannins per 50 µL reaction volume. Concentrations of polyphenols discussed above can be extrapolated to other polyphenol-containing samples.

Assays to determine the level of inhibitory substances in a sample and resistance of a polymerase are known in the art. For example, polyphenolic content can be assessed according to volumetric titration (e.g., oxidizing agent such as permanganate), colorimetric assay (e.g., Porter's Assay, Folin-Ciocalteu reaction), antioxidant capacity of a fraction (e.g., TEAC assay, DPPH assay, ORAC assay, FRAP assay, lipoprotein oxidation inhibition assay), biosensor, or diode array detector-coupled HPLC.

Urine.

In some embodiments, a mutant polymerase described herein can amplify a target nucleic acid in the presence of urine, a known PCR inhibitor. A mutant polymerase can be used to amplify a DNA target in a real-time PCR of a DNA target in the presence of urine. A mutant polymerase can be used in combination with an enzyme having reverse transcriptase activity to amplify an RNA target in a real-time reverse transcriptase (RT) PCR of an RNA target in the presence of urine.

A mutant polymerase described herein can provide for amplification of a target nucleic acid in a sample containing urine at a level inhibitory to a wild type Taq, Klentaq, Omni Taq, or Omni Klentaq.

In some embodiments, a mutant polymerase can display amplification activity in PCR assays (e.g., end point or real-time PCR) containing up to about 90% urine. For example, urine can be present in an assay mixture comprising a mutant polymerase described herein at about 1%, 10%, 20%, 30%, 40%, 50%, 60%, 70%, 80%, or 90%.

GITC.

In some embodiments, a mutant polymerase described herein can amplify a target nucleic acid in the presence of guanidinium thiocyanate (GITC) (also known as guanidine thiocyanate), a known PCR inhibitor. GITC) is a chaotropic agent commonly used in the extraction of DNA or RNA. GITC can be present in a sample after using a GITC-phenol-chloroform extraction method.

A mutant polymerase can be used to amplify a DNA target in a real-time PCR of a DNA target in the presence of GITC. A mutant polymerase can be used in combination with an enzyme having reverse transcriptase activity to amplify an RNA target in a real-time reverse transcriptase (RT) PCR of an RNA target in the presence of GITC.

A mutant polymerase described herein can provide for amplification of a target nucleic acid in a sample containing GITC at a level inhibitory to a wild type Taq, Klentaq, Omni Taq, or Omni Klentaq.

In some embodiments, a mutant polymerase can display amplification activity in PCR assays (e.g., end point or real-time PCR) containing up to about 200 mM GITC. For example, GITC can be present in an assay mixture comprising a mutant polymerase described herein at about 1 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM.

Ethanol.

In some embodiments, a mutant polymerase described herein can amplify a target nucleic acid in the presence of ethanol, a known PCR inhibitor. A mutant polymerase can be used to amplify a DNA target in a real-time PCR of a DNA target in the presence of ethanol. A mutant polymerase can be used in combination with an enzyme having reverse transcriptase activity to amplify an RNA target in a real-time reverse transcriptase (RT) PCR of an RNA target in the presence of ethanol.

A mutant polymerase described herein can provide for amplification of a target nucleic acid in a sample containing ethanol at a level inhibitory to a wild type Taq, Klentaq, Omni Taq, or Omni Klentaq.

In some embodiments, a mutant polymerase can display amplification activity in PCR assays (e.g., end point or real-time PCR) containing up to about 10% ethanol. For example, ethanol can be present in an assay mixture comprising a mutant polymerase described herein at about 1%, 2%, 3%, 4%, 5%, 6%, 7%, 8%, 9% or 10%.

Food.

In some embodiments, a mutant polymerase described herein can amplify a target nucleic acid in the presence of food samples containing an inhibitory substance. A mutant polymerase can be used to amplify a DNA target in a real-time PCR of a DNA target in the presence of ethanol. A mutant polymerase can be used in combination with an enzyme having reverse transcriptase activity to amplify an RNA target in a real-time reverse transcriptase (RT) PCR of an RNA target in the presence of ethanol.

Food samples known to contain inhibitory substances (e.g., polyphenols) include, but are not limited to, chocolate, peanut buffer, milk, seafood, meat, egg, potato skins, tea, berries, beer, wine, olive oil, walnuts, peanuts, or other plant material including fruits, vegetables, or tubers.

For example, a wild type Taq polymerase (SEQ ID NO: 1) is completely inhibited at a chocolate concentration of more than about 0.04 µg/µl chocolate in a sample while other polymerases, such as Omni Taq (SEQ ID NO: 3) or Omni Klentaq (SEQ ID NO: 4) can tolerate about 5 µg/µl chocolate. In contrast, a mutant polymerase described herein can maintain polymerase activity even where a chocolate concentration exceeds more than about 5 µg/µl chocolate (more than about 5, 10, or 15 µg/µl chocolate) in a sample. As another example, an assay mixture containing a mutant polymerase described herein can contain a concentration of chocolate up to about 20 µg/µl. As another example, an assay mixture containing a mutant polymerase described herein can contain a concentration of chocolate at least about 0.05 µg/µl up to about 20 µg/µl.

PCR

A mutant polymerase (including all variants thereof) described herein can be used in a variety of polymerase reactions known to the art (see e.g., Dorak (2006) Real-Time PCR, Taylor & Francis, ISBN 041537734x; Bustin, ed. (2004) A-Z of Quantitative PCR, International University Line, ISBN 0963681788; King and O'Connel (2002) RT-PCR Protocols, 1$^{st}$ Ed., Human Press, ISBN-10 0896038750). For example, a mutant polymerase can be employed in PCR reactions, primer extension reactions, etc.

For example, a mutant polymerases described herein can be used in nucleic acid amplification processes (either alone or in combination with one or more other enzymes), such as Allele-specific PCR; Assembly PCR or Polymerase Cycling Assembly; Asymmetric PCR; Linear-After-The-Exponential-PCR; Helicase-dependent amplification; Hot-start PCR; Intersequence-specific PCR; Inverse PCR; Ligation-mediated PCR; Methylation-specific PCR; Miniprimer PCR; Multiplex Ligation-dependent Probe Amplification; Multiplex-PCR; Nested PCR; Overlap-extension PCR; Quantitative PCR; Quantitative End-Point PCR; Quantitative Real-Time PCR; RT-PCR (Reverse Transcription PCR); Solid Phase PCR; Thermal asymmetric interlaced PCR; Touchdown PCR; PAN-AC; Universal Fast Walking; Long PCR; Rapid Amplified Polymorphic DNA Analysis; Rapid Amplification of cDNA Ends (RACE); Differential Display PCR; In situ PCR; High-Fidelity PCR; PCR or DNA Sequencing (cycle sequencing).

A target nucleic acid of a sample can be any target nucleic acid of interest. For example, a target nucleic acid can be a deoxyribonucleic acid (DNA), a ribonucleic acid (RNA), or an artificial nucleic acid analog (e.g., a peptide nucleic acid, morpholino- and locked nucleic acid, glycol nucleic acid, or threose nucleic acid).

A primer is understood to refer to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A target nucleic acid, e.g., a template DNA molecule, is understood to be a strand of a nucleic acid from which a complementary nucleic acid strand can be synthesized by a DNA polymerase, for example, in a primer extension reaction.

In some embodiments, the use of a mutant polymerase enzyme described herein does not require any, or substantial, changes in the typical protocol, but can allow, for example, for the presence of higher concentrations of inhibitory substances. A mutant polymerase described herein, and methods for use thereof, can allow for elimination or substantial elimination of an enrichment step for sample preparation. Eliminating an enrichment step can significantly reduce the time to detection or quantification.

A mutant polymerase described herein can be used in an end-point PCR. For example, end-point PCR is commonly carried out in a reaction volume of about 10-200 µl in small reaction tubes (about 0.2-0.5 ml volumes) in a thermal cycler.

A mutant polymerase described herein can be used with a variety of commercially available end-point PCR kits. The use of a mutant polymerase enzyme described herein generally does not require any, or substantial, changes in the typical end-point PCR protocol, but can allow, for example, a sample having a higher amount of an inhibitory substance.

A mutant polymerase described herein can be used in real-time PCR (also known as a quantitative polymerase chain reaction (qPCR)). For example, a mutant polymerase described herein can be used in a real-time PCR assay featuring a non-specific fluorescent dye (e.g., a fluorochrome) that can intercalate with any double-stranded DNA. With a non-specific fluorescent dye, an increase in DNA product during PCR can lead to an increase in fluorescence intensity and is measured at each cycle, thus allowing DNA concentrations to be quantified.

As another example, a mutant polymerase described herein can be used in a real-time PCR assay featuring a hybridization probe. As another example, a mutant polymerase described herein can be used in a real-time PCR multiplex assay featuring a hybridization probe. A hybridization probe can be a sequence-specific DNA probe including a fluorescent reporter at one end and a quencher of fluorescence at the opposite end of the probe, where break down of the probe by a 5' to 3' exonuclease activity of a polymerase can break the reporter-quencher proximity and thus allow unquenched emission of fluorescence, which can be detected after excitation with a laser (e.g., a TaqMan® assay). With a hybridization probe, an increase in the product targeted by the reporter probe at each PCR cycle can cause a proportional increase in fluorescence due to the breakdown of the probe and release of the reporter. A mutant polymerase described herein can be used with a variety of commercially available real-time PCR kits.

Thus, methods described herein can be applied to improve the nucleic acid detection in an end-point PCR or a real-time PCR.

In some embodiments, a mutant polymerase described herein can be used in combination with an enzyme having reverse transcriptase activity in a real-time reverse transcriptase (RT) PCR amplification of an RNA target. It is noted that reverse transcriptase (RT) PCR is not to be confused with real-time polymerase chain reaction (Q-PCR), which is sometimes (incorrectly) abbreviated as RT-PCR in the art. In RT-PCR, an RNA strand is first reverse transcribed into its DNA complement (complementary DNA, or cDNA) using the enzyme reverse transcriptase, and the resulting cDNA is amplified using traditional PCR. Like with end-point PCR, conventional RT-PCR protocols require extensive purification steps prior to amplification to purify RNA from inhibitors and ribonucleases, which can destroy the RNA template. Both the inhibition and degradation of RNA are major concerns in important clinical and diagnostics tests, which may lead to false-negative results.

The buffer for use in the various PCR assay mixtures described herein is generally a physiologically compatible buffer that is compatible with the function of enzyme activities and enables cells or biological macromolecules to retain their normal physiological and biochemical functions. Typically, a physiologically compatible buffer will include a buffering agent (e.g., TRIS, MES, $PO_4$, HEPES, etc.), a chelating agent (e.g., EDTA, EGTA, or the like), a salt (e.g., ammonium sulfate, NaCl, KCl, $MgCl_2$, $CaCl_2$, NaOAc, KOAc, $Mg(OAc)_2$, etc.) and optionally a stabilizing agent (e.g., sucrose, glycerine, Tween20, etc.).

Various PCR additives and enhancers can be employed with the methods described herein. For example, betaine (e.g., MasterAmp™ 10×PCR, Epicentre Biotechnologies) can be added to the PCR assay, to further aid in overcoming the inhibition by inhibitory substances described herein. Betaine can be included at final concentration about 1 M to about 2M. Generally, betaine alone is insufficient to overcome the inhibition of various inhibitory substances described herein when used with conventional DNA polymerases.

As another example, a mutant polymerase described herein can be used in conjunction with a PCR enhancer described in US Pat Pub No. 2012/0028259 or WO 2012/088479, each incorporated herein by reference. For example, a mutant polymerase can be used in conjunction with a PCR enhancer including trehalose (e.g., about 0.1 to about 1.0 M D-(+)-trehalose per amplification reaction mixture volume), carnitine (about 0.1 to about 1.5 M L-carnitine per amplification reaction mixture volume), or a non-ionic detergent (e.g., Brij-58, NP-40, Nonidet P-40, Igepal CA-630, Brij-58, Tween-20, NP-40, or Triton X-100 at about 0.01% to about 8% non-ionic detergent per amplification reaction mixture volume) or optionally one or more of heparin (e.g., an amount of heparin equivalent to about 2 units to about 50 units heparin per mL of whole blood, plasma, or serum in an amplification reaction mixture), casein (at least about 0.05% up to about 2.5% per amplification reaction mixture volume), or polyvinylpyrrolidone (PVP) or a modified polymer of PVP (PVPP) (e.g., about 0.1% up to about 25%). As another example, a mutant polymerase can be used in conjunction with a PCR enhancer including about 0.6 M trehalose per amplification reaction mixture volume; about 0.5 M carnitine per amplification reaction mixture volume; or a non-ionic detergent (e.g., a polyoxyethylene cetyl ether at about 0.04% to about 0.2% or a nonyl phenoxylpolyethoxylethanol at about 0.4% to about 0.8% per amplification reaction mixture volume); or optional heparin at about 10 units per mL of whole blood, blood fraction, plasma, or serum.

As another example, a mutant polymerase described herein can be used in conjunction with commercially available PCR amplification reaction enhancers, such as MasterAmp™ 10×PCR Enhancer, Epicentre Biotechnologies; TaqMaster PCR Enhancer, MasterTaq Kit, PCR Extender System, 5 PRIME GmbH; Hi-Spec Additive, Bioline; PCRboost™, Biomatrica®; PCRX Enhancer System, Invitrogen; Taq Extender™ PCR Additive, Perfect Match® PCR Enhancer, Stratagene; Polymer-Aide PCR Enhancer, Sigma-Aldrich.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a mutant polymerase described herein or a nucleic acid encoding such mutant polymerase or, optionally, a primer, a buffer, or other composition or component (e.g., a magnesium salt) necessary or helpful for PCR. Such packaging of the components separately can, if desired, be presented in a pack or dispenser device which may contain one or more assay unit forms containing a composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy.

Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

Compositions and methods described herein utilizing molecular biology protocols can be according to a variety of standard techniques known to the art (see, e.g., Sambrook and Russell (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russell (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363;

Baneyx (2004) Protein Expression Technologies, Taylor & Francis, ISBN-10: 0954523253).

A mutation refers to a change introduced into a parental sequence, including, but not limited to, substitutions, insertions, or deletions (including truncations). The consequences of a mutation include, but are not limited to, the creation of a new character, property, function, phenotype or trait not found in the protein encoded by the parental sequence.

Enzyme activity refers to the specificity and efficiency of a DNA polymerase. Enzyme activity of a DNA polymerase can also be referred to as polymerase activity, which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer. The reaction mixtures can be incubated at, e.g., 74 C and stopped by cooling to, e.g., 40 C and adding ice-cold EDTA. An aliquot can be removed from each reaction mixture. Unincorporated radioactively labeled dCTP can be removed from each aliquot by gel filtration (e.g., Centri-Sep, Princeton Separations, Adelphia, N.J.). The column eluate can be mixed with scintillation fluid. Radioactivity in the column eluate can be quantified with a scintillation counter to determine the amount of product synthesized by the polymerase. One unit of polymerase activity can be defined as the amount of polymerase necessary to synthesize 10 nmole of product in 30 minutes (see e.g., Lawyer et al. 1989 J. Biol. Chem. 264, 6427-647). Other methods of measuring polymerase activity are known in the art (see e.g. Sambrook and Russell (2001) Molecular Cloning: A Laboratory Manual, 3d ed., Cold Spring Harbor Laboratory Press, ISBN-10: 0879695773).

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct.

These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

Design, generation, and testing of the variant polynucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide or polypeptide variants having, for example, at least 95-99% identity to the reference sequence described herein and screen such for desired phenotypes according to methods routine in the art.

Nucleotide amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. Conversely, recitation of discrete values is understood to include a range between each of the recited discrete values.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

The following example shows performance of the H101 (SEQ ID NO: 14) Klentaq mutant with crude samples containing chocolate or black pepper.

A 380 bp rRNA target was amplified from 1 ng bacterial DNA in 50 μl reactions with 15 U Klentaq 1, w.t. Taq (New England Biolabs), and the Klentaq1 mutant H101 (SEQ ID NO: 14) in the presence of 0, 3, 4, 5, 6 and 9 μl of a crude black pepper extract (see e.g., FIG. 1, 50 mg/ml, top panel), or 0, 2, 2.5, 3.0, 3.5 and 4.5 μl 10% chocolate suspension (see e.g., FIG. 1, bottom panel), lanes 1-6. The amplified products were analyzed in ethidium bromide stained agarose gel.

Results showed that the H101 (SEQ ID NO: 14) mutant DNA polymerase outperformed both wild type Taq and truncated Klentaq1 while remaining functional in all concentrations of the food related PCR inhibitors tested (see e.g., FIG. 1).

Example 2

The following example shows resistance of B-9 (SEQ ID NO: 5) and H101 (SEQ ID NO: 14) Klentaq mutants to black pepper inhibition.

A 350 bp bacterial 16S rRNA target was amplified from 1 ng bacterial DNA with 0.8 μl purified Omni Klentaq (OKT) and Klentaq mutants H101 (SEQ ID NO: 14) and B-9 (SEQ ID NO: 5), in the presence of 0, 3, 4, 5, 6 and 7 μl 10% black pepper extract (see e.g., FIG. 2, left to right, six reactions per enzyme) in 35 ul reactions. No PCR enhancer was used in the reactions.

Figure 2:
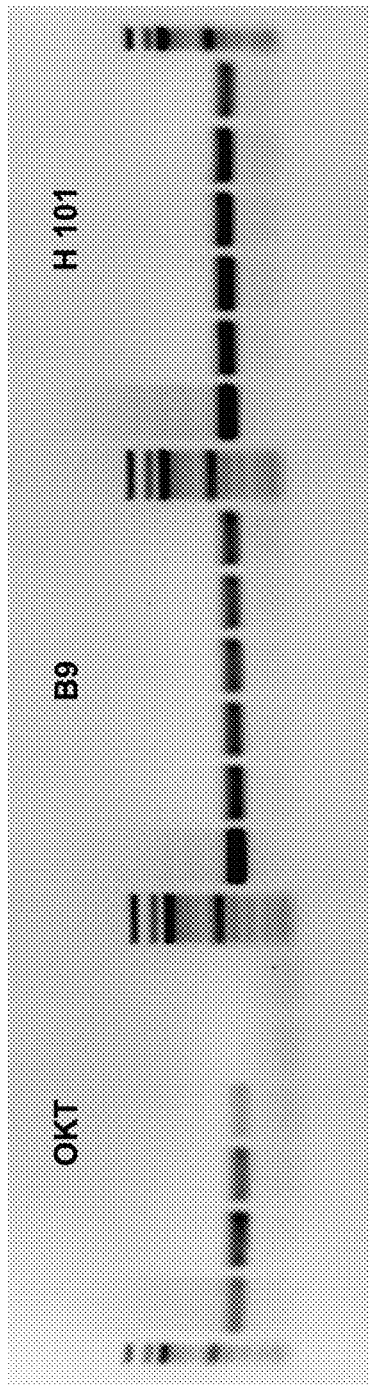
FIG. 2 is an image of a gel showing resistance of B-9 (SEQ ID NO: 5) and H101 (SEQ ID NO: 14) Klentaq mutants to black pepper inhibition. A 350 bp bacterial 16S rRNA target was amplified from 1 ng bacterial DNA with 0.8 µl purified Omni Klentaq (OKT) and Klentaq mutants H101 (SEQ ID NO: 14) and B-9 (SEQ ID NO: 5), in the presence of 0, 3, 4, 5, 6 and 7 µl 10% black pepper extract (left to right, six reactions per enzyme) in 35 ul reactions. Further details regarding methodology are available in Example 2.

Results showed the B-9 (SEQ ID NO: 5) and H101 (SEQ ID NO: 14) mutants had higher resistance than Omni Klentaq to black pepper inhibition (see e.g., FIG. 2).

Example 3

The following example shows resistance of B-9 (SEQ ID NO: 5) and H101 (SEQ ID NO: 14) Klentaq mutants to chocolate inhibition.

Figure 3:
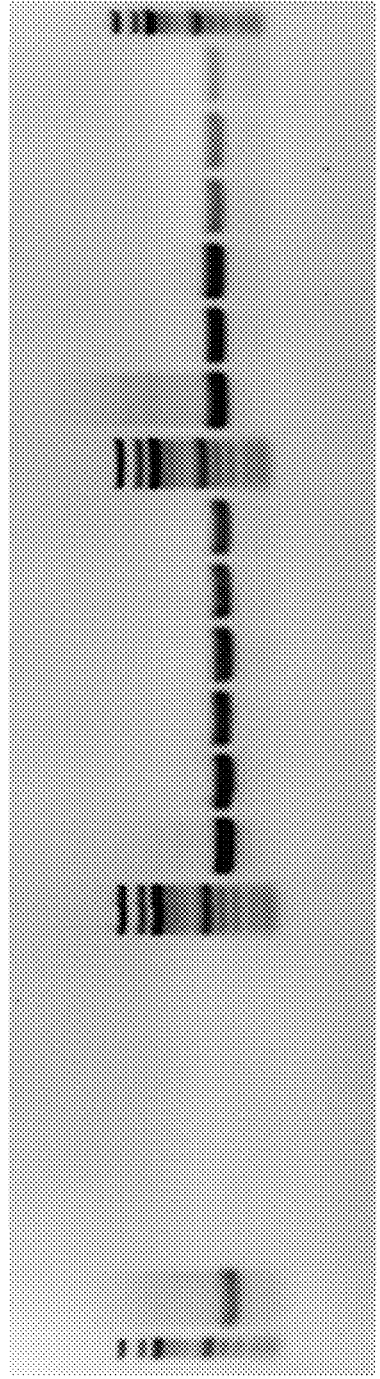
FIG. 3 is an image of gel showing resistance of B-9 (SEQ ID NO: 5) and H101 (SEQ ID NO: 14) Klentaq mutants to chocolate inhibition. A 350 bp bacterial 16S rRNA target was amplified in 35 ul reactions from 1 ng bacterial DNA with 0.8 µl purified Omni Klentaq (OKT) and Klentaq mutants H101 (SEQ ID NO: 14) and B-9 (SEQ ID NO: 5) in the presence of 0, 2, 2.5, 3, 3.5 and 4 µl 10% chocolate (left to right, six reactions per enzyme). Further details regarding methodology are available in Example 3.

A 350 bp bacterial 16S rRNA target was amplified in 35 ul reactions from 1 ng bacterial DNA with 0.8 μl purified Omni Klentaq (OKT) and Klentaq mutants H101 (SEQ ID NO: 14) and B-9 (SEQ ID NO: 5) in the presence of 0, 2, 2.5, 3, 3.5 and 4 μl 10% chocolate (see e.g., FIG. 3, left to right, six reactions per enzyme). No PCR enhancer was used in the reactions.

Results showed that the B-9 (SEQ ID NO: 5) and H101 (SEQ ID NO: 14) mutants had higher resistance than Omni Klentaq to chocolate inhibition (see e.g., FIG. 3).

Example 4

The following example shows resistance of C-12 (SEQ ID NO: 10) full-length Taq mutant to chocolate inhibition.

Figure 4:
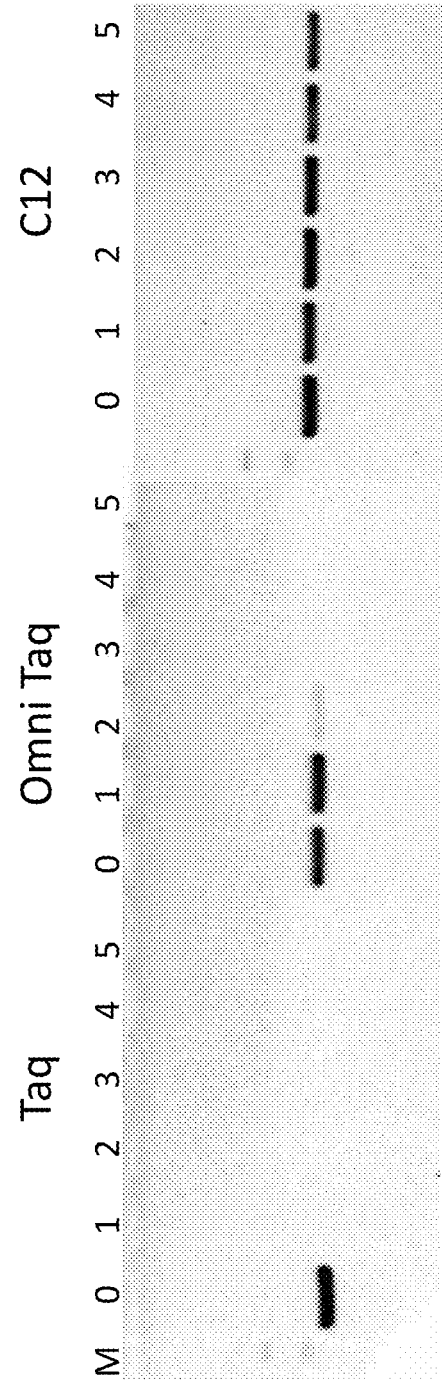
FIG. 4 is an image of a gel showing resistance of C-12 (SEQ ID NO: 10) full-length Taq mutant to chocolate inhibition. A 346 bp 16S rRNA target was amplified in 35 ul reactions from 350 pg of E. coli DNA with 0.8 µl purified OmniTaq, mutant C-12 (SEQ ID NO: 10), or wild type Taq (NEB) with 0, 1, 2, 3, 4 or 5 uL of a 10% chocolate extract. Further details regarding methodology are available in Example 4.

A 346 bp 16S rRNA target was amplified in 35 ul reactions from 350 pg of *E. coli* DNA with 0.8 μl purified OmniTaq, mutant C-12 (SEQ ID NO: 10), or wild type Taq (NEB) with 0, 1, 2, 3, 4 or 5 uL of a 10% chocolate extract (see e.g., FIG. 4).

Results showed that C-12 (SEQ ID NO: 10) had activity at 5 μl of chocolate extract, while OmniTaq was partially inhibited at 2 μl and completely inhibited at 4 μl chocolate. Taq was inactivated at only 1 μl of chocolate.

Example 5

The following example shows resistance of C-12 (SEQ ID NO: 10) full-length Taq mutant to black pepper inhibition.

Figure 5:
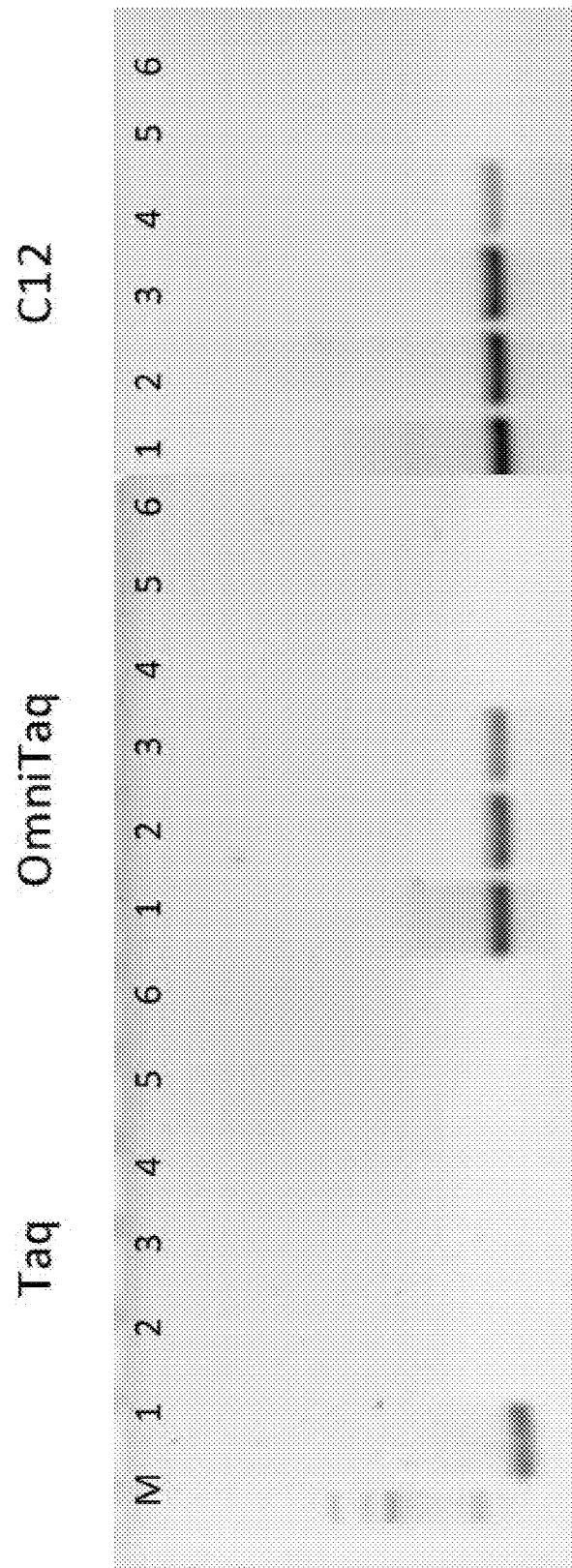
FIG. 5 is an image of a gel showing resistance of C-12 (SEQ ID NO: 10) full-length Taq mutant to black pepper inhibition. A 346 bp 16S rRNA target was amplified in 35 ul reactions from 350 pg of E. coli DNA with 0.8 µl of purified OmniTaq, mutant C-12 (SEQ ID NO: 10), or wild-type Taq (NEB) with 0, 0.25, 0.5, 1, 2 or 4 µl of black pepper extract at 500 mg/mL (Lanes 1-6). Further details regarding methodology are available in Example 5.
Figure 6:
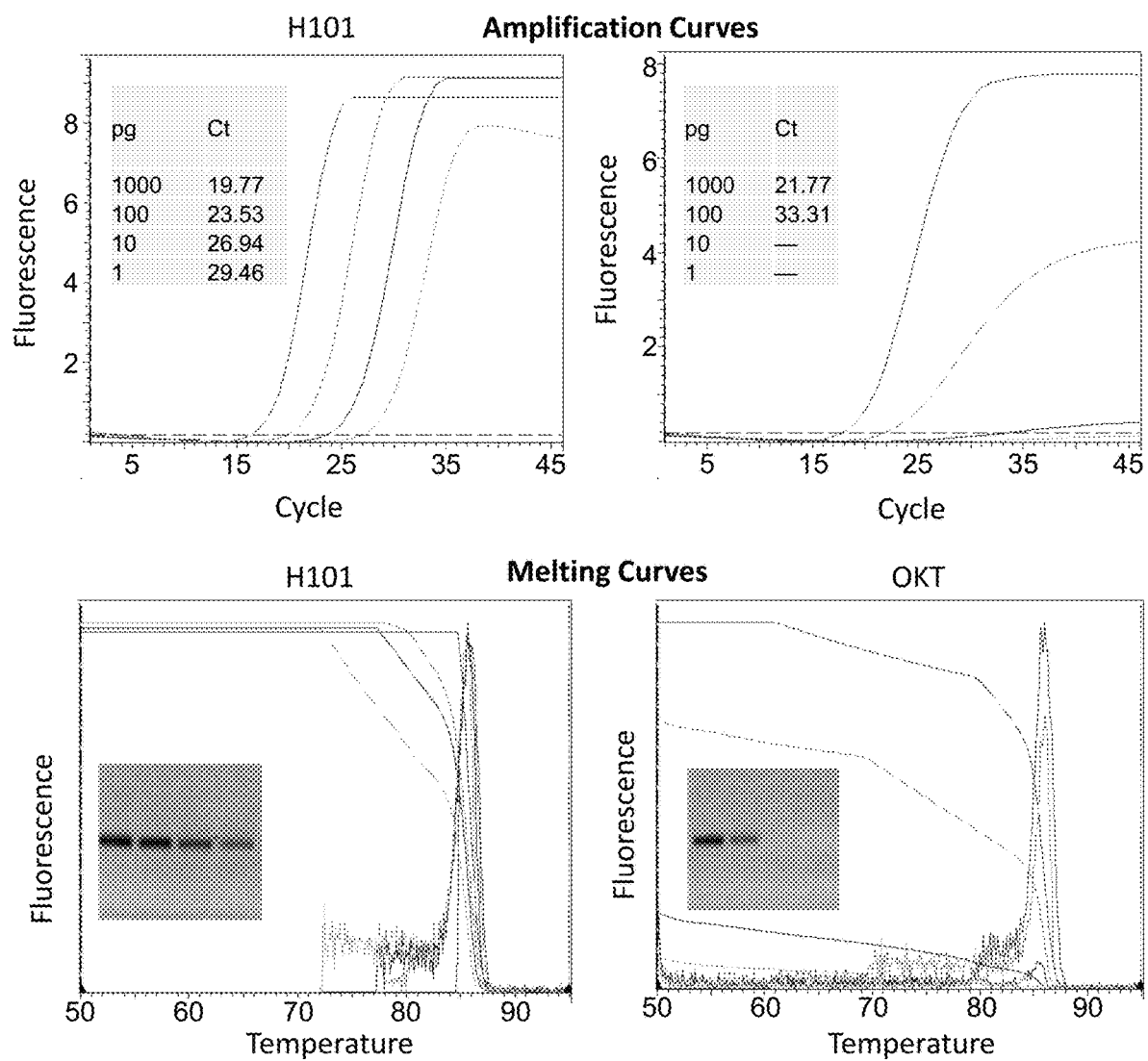
FIG. 6 is a series of amplification curves and melting curves showing resistance of H101 (SEQ ID NO: 14) Klentaq mutant to chocolate in qPCR (SYBR Green). Salmonella DNA was 10-fold serially diluted from 1,000 pg to 1 pg and it was detected by qPCR with SYBR Green with primer HiLA-3. The reactions included 0.6 µl of purified Omni KlenTaq (OKT) or mutant H101 (SEQ ID NO: 14) with 2 µl 10% chocolate extract per 35 µl reaction. Further details regarding methodology are available in Example 6.

A 346 bp 16S rRNA target was amplified in 35 ul reactions from 350 pg of *E. coli* DNA with 0.8 μl of purified OmniTaq, mutant C-12 (SEQ ID NO: 10), or wild-type Taq (NEB) with 0, 0.25, 0.5, 1, 2 or 4 μl of black pepper extract at 500 mg/mL (see e.g., FIG. 5, Lanes 1-6).

Results showed that the C-12 (SEQ ID NO: 10) mutant showed activity at 1 μl of pepper extract while Omni Taq was completely inhibited at that concentration. Taq was inactivated at only 0.25 µl black pepper Example 6

The following example shows resistance of H101 (SEQ ID NO: 14) Klentaq mutant to chocolate in qPCR (SYBR Green).

Salmonella DNA was 10-fold serially diluted from 1,000 pg to 1 pg and it was detected by qPCR with SYBR Green with primer HiLA-3. The reactions included 0.6 µl of purified Omni KlenTaq (OKT) or mutant H101 (SEQ ID NO: 14) with 2 µl 10% chocolate extract per 35 µl reaction.

Results showed that the H101 (SEQ ID NO: 14) mutant had resistance to chocolate while OKT was strongly inhibited.

Example 7

The following example shows resistance of C-12 (SEQ ID NO: 10) full-length Taq mutant to chocolate in qPCR (SYBR Green).

Figure 7:
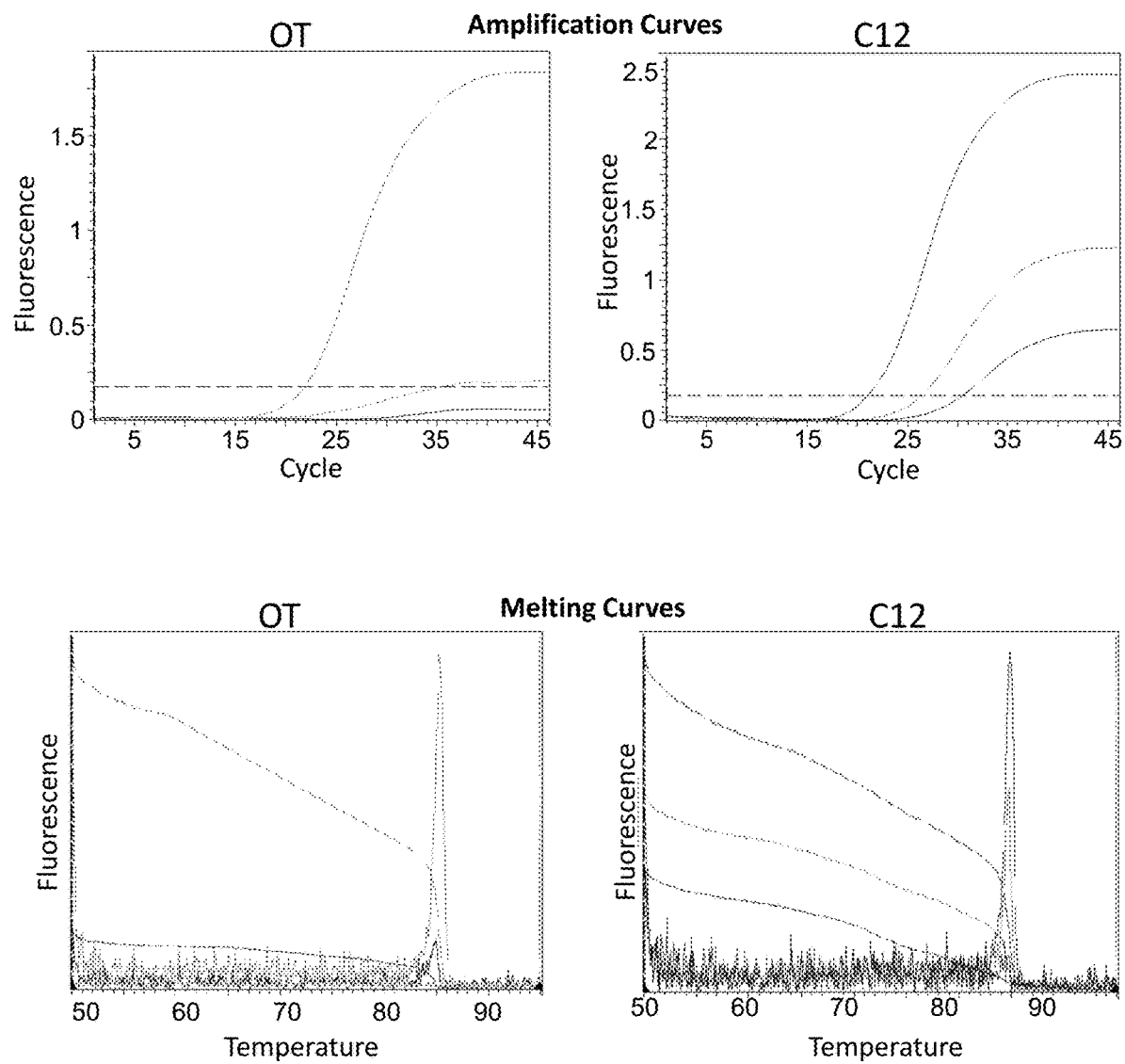
FIG. 7 is a series of amplification curves and melting curves showing resistance of C-12 (SEQ ID NO: 10) full-length Taq mutant to chocolate in qPCR (SYBR Green). Salmonella DNA was 10-fold serially diluted from 100 pg to 1 pg and detected by qPCR with SYBR Green with primer HiLA-3. The reactions included 0.3 µl of purified OmniTaq (OT) and 0.3 μl of the C-12 (SEQ ID NO: 10) mutant with 2 μL 10% chocolate extract per 35 μl reaction. Further details regarding methodology are available in Example 7.

Salmonella DNA was 10-fold serially diluted from 100 pg to 1 pg and detected by qPCR with SYBR Green with primer HiLA-3. The reactions included 0.3 µl of purified OmniTaq (OT) and 0.3 µl of the C-12 (SEQ ID NO: 10) mutant with 2 µL 10% chocolate extract per 35 µl reaction (see e.g., FIG. 7).

Results showed that the C-12 (SEQ ID NO: 10) mutant had a higher resistance to chocolate while OT was strongly inhibited.

Example 8

The following example shows performance of the H101 (SEQ ID NO: 14) Klentaq mutant in PCR with crude samples containing whole blood.

Figure 8:
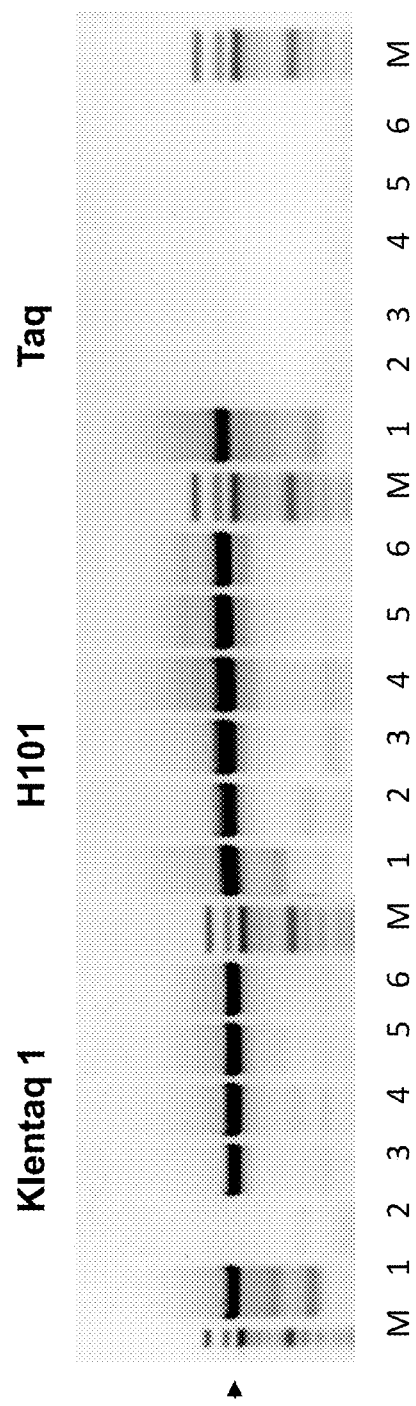
FIG. 8 is an image of a gel showing performance of the H101 (SEQ NO: 14) Klentaq mutant in PCR with crude samples containing whole blood. A 1.1 kb target from the human CCR5 gene was amplified in 25 μl reactions with 10 U Klentaq1, w.t. Taq (New England Biolabs), and the H101 (SEQ ID NO: 14) Klentaq1 mutant from 40%, 20%, 10%, 5%, and 2.5% heparin treated blood, lanes 1-6, respectively. Lane 1 (positive controls) contained no blood, but 10 ng human DNA. Lane M, DNA ladder. The amplified products were analyzed in ethidium bromide stained agarose gel. Further details regarding methodology are available in Example 8.

A 1.1 kb target from the human CCR5 gene was amplified in 25 µl reactions with 10 U Klentaq1, w.t. Taq (New England Biolabs), and the H101 (SEQ ID NO: 14) Klentaq1 mutant from 40%, 20%, 10%, 5%, and 2.5% heparin treated blood, lanes 1-6, respectively. Lane 1 (positive controls) contained no blood, but 10 ng human DNA (see e.g., FIG. 8). The amplified products were analyzed in ethidium bromide stained agarose gel.

Results showed that the H101 (SEQ ID NO: 14) mutant polymerase outperformed both the wild type Taq and its truncated version, Klentaq1, where the H101 (SEQ ID NO: 14) mutant showed higher resistance to the blood inhibition.

Example 9

The following example shows performance of the H101 (SEQ ID NO: 14) Klentaq mutant in PCR with crude samples containing humic acid.

Figure 9:
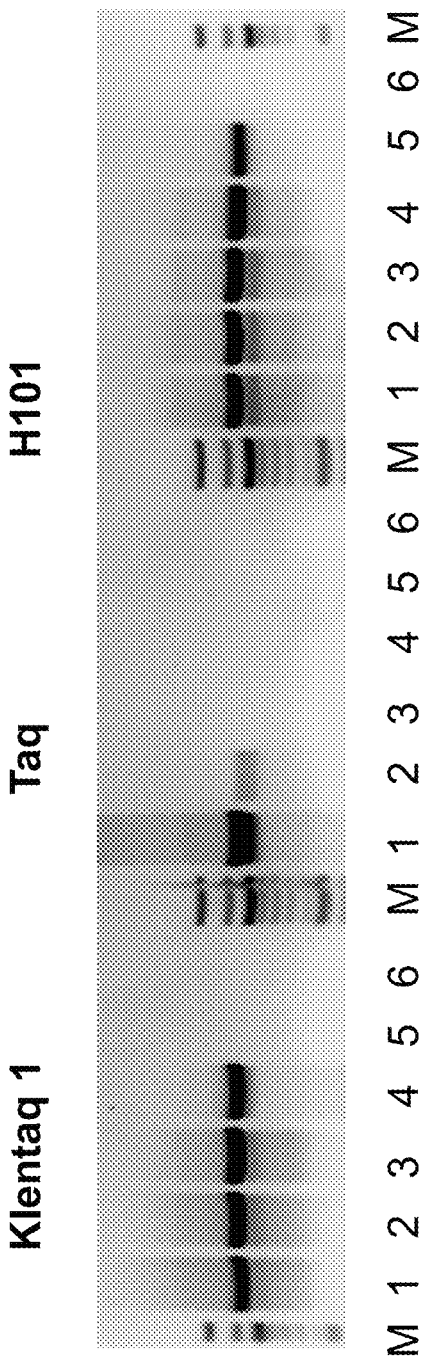
FIG. 9 is an image of a gel showing performance of the H101 (SEQ ID NO: 14) Klentaq mutant in PCR with crude samples containing humic acid. A 1.1 kb target from the human CCR5 gene was amplified from 10 ng human DNA in 25 ul reactions with 5 U Klentaq1, w.t. Taq (New England Biolabs), and the H101 (SEQ ID NO: 14) Klentaq1 mutant in the presence of 0, 12, 25, 50, 100 and 200 ng humic acid (approximate amounts), lanes 1-6, respectively. Lanes M, DNA ladder. Further details regarding methodology are available in Example 9.

A 1.1 kb target from the human CCR5 gene was amplified from 10 ng human DNA in 25 ul reactions with 5 U Klentaq1, w.t. Taq (New England Biolabs), and the H101 (SEQ ID NO: 14) Klentaq1 mutant in the presence of 0, 12, 25, 50, 100 and 200 ng humic acid (approximate amounts) (see e.g., FIG. 9, lanes 1-6, respectively. The amplified products were analyzed in ethidium bromide stained agarose gel.

Results showed that the H101 (SEQ ID NO: 14) mutant polymerase outperformed both the wild type Taq and its truncated version, Klentaq1, where H101 (SEQ ID NO: 14) showed higher resistance to the PCR inhibitor humic acid.

Example 10

The following example shows resistance of Klentaq mutants to bile inhibition.

Figure 10:
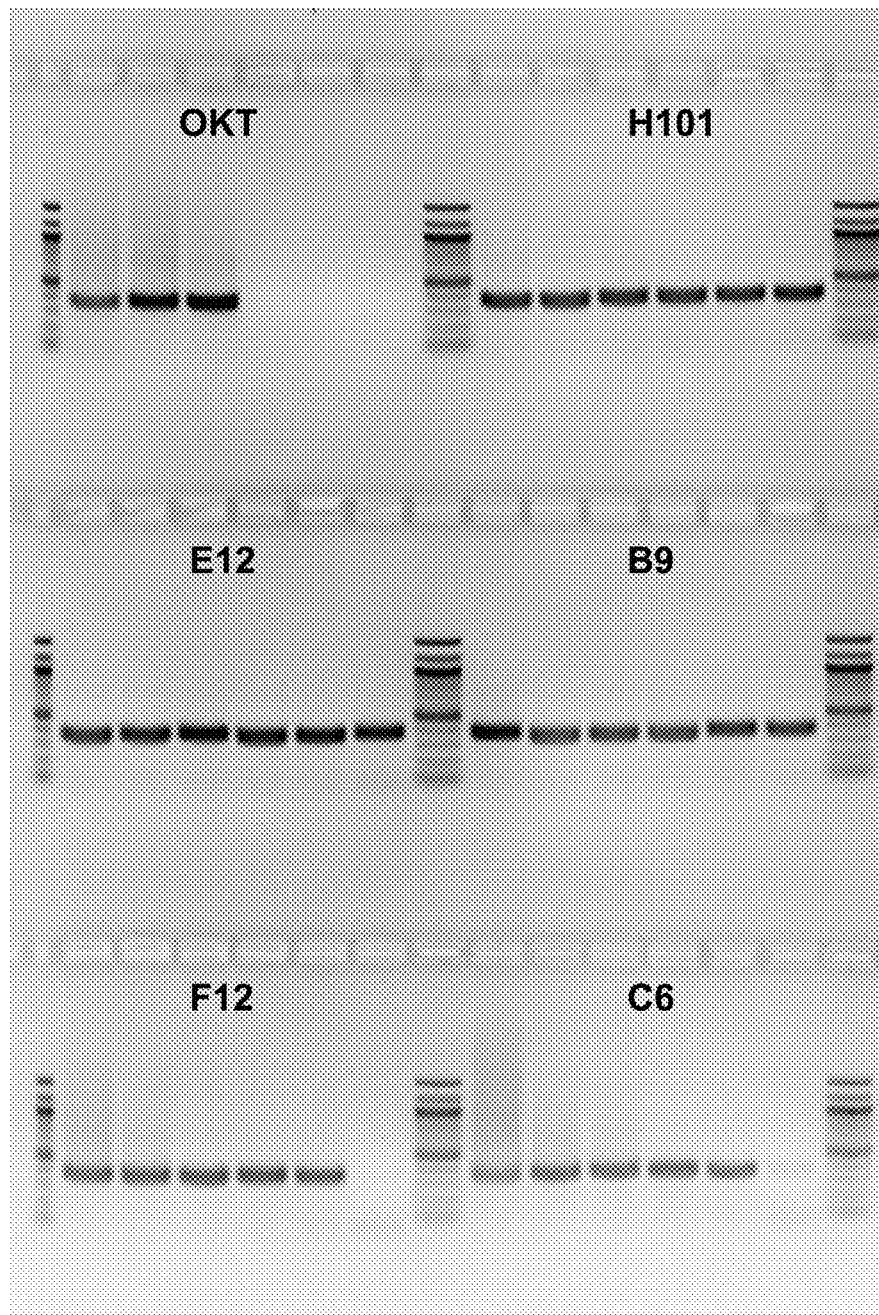
FIG. 10 is a series of gel images showing resistance of Klentaq mutants to bile inhibition. A 350 bp bacterial 16S rRNA target was amplified from 1 ng bacterial DNA in 50 μl reactions with 0.5 ul purified Omni Klentaq (OKT) or the Klentaq mutants H101 (SEQ ID NO: 14), E-12 (SEQ ID NO: 8), B-9 (SEQ ID NO: 5), F-12 (SEQ ID NO: 7), and C-6 (SEQ ID NO: 9), in the presence of 0, 0.4, 0.8, 1.2, 1.6 and 2 ul bile salts extract (left to right, six reactions per enzyme). Further details regarding methodology are available in Example 10.

A 350 bp bacterial 16S rRNA target was amplified from 1 ng bacterial DNA in 50 µl reactions with 0.5 ul purified Omni Klentaq (OKT) or the Klentaq mutants H101 (SEQ ID NO: 14), E-12 (SEQ ID NO: 8), B-9 (SEQ ID NO: 5), F-12 (SEQ ID NO: 7), and C-6 (SEQ ID NO: 9), in the presence of 0, 0.4, 0.8, 1.2, 1.6 and 2 ul bile salts extract (see e.g., FIG. 10, left to right, six reactions per enzyme). No PCR enhancer was used in the reactions.

Results showed that all tested mutant polymerases showed higher than Omni Klentaq resistance to bile inhibition.

Example 11

The following example shows performance of H101 (SEQ ID NO: 14) Klentaq mutant in PCR with crude samples containing plant tissue extract.

Figure 11:
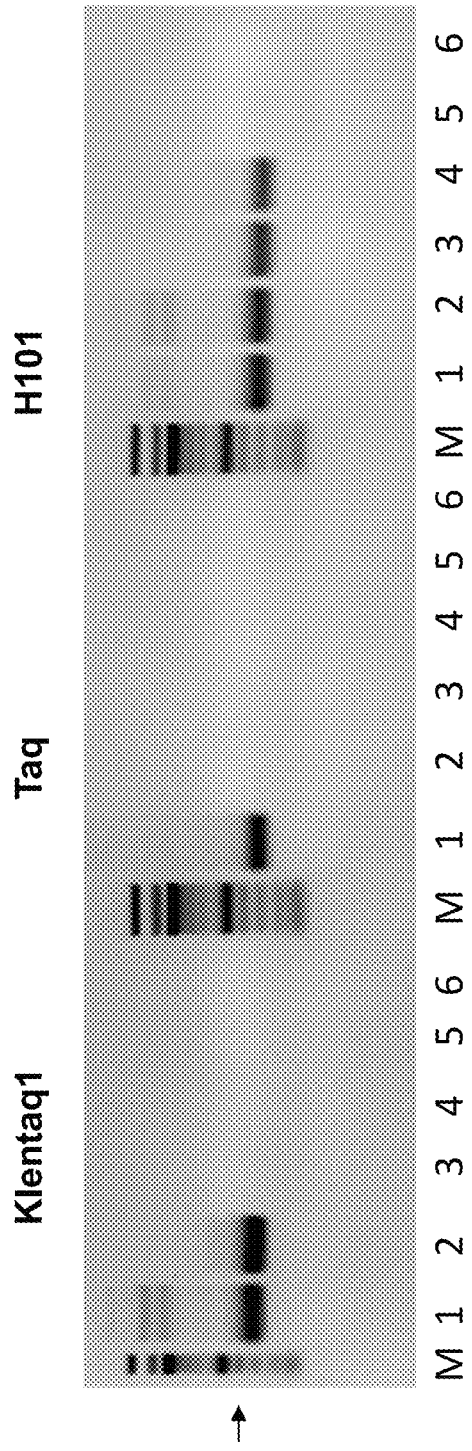
FIG. 11 is an image of a gel showing performance of H101 (SEQ ID NO: 14) Klentaq mutant in PCR with crude samples containing plant tissue extract. A 320 bp target from the beta-actin gene was amplified from 10 ng human DNA in 50 μl reactions with 10 U Klentaq 1, w.t. Taq (New England Biolabs), and the H101 (SEQ ID NO: 14) Klentaq1 mutant in the presence of 0, 0.5, 1.0, 1.5, 2.0 and 2.5 μl of a crude plant leaf extract (lanes 1-6). Lanes M, DNA ladder. Further details regarding methodology are available in Example 11.

A 320 bp target from the beta-actin gene was amplified from 10 ng human DNA in 50 µl reactions with 10 U Klentaq 1, w.t. Taq (New England Biolabs), and the H101 (SEQ ID NO: 14) Klentaq1 mutant in the presence of 0, 0.5, 1.0, 1.5, 2.0 and 2.5 µl of a crude plant leaf extract (see e.g., FIG. 11, lanes 1-6). The amplified products were analyzed in ethidium bromide stained agarose gel.

Results showed that the H101 (SEQ ID NO: 14) mutant DNA polymerase outperformed both the wild type Taq and its truncated version, Klentaq1, where H101 (SEQ ID NO: 14) showed higher resistance to the PCR inhibitors in the plant tissue.

Example 12

The following example shows resistance of full-length Taq mutant C-66 (SEQ ID NO: 11) to shrimp meat inhibition.

Figure 12:
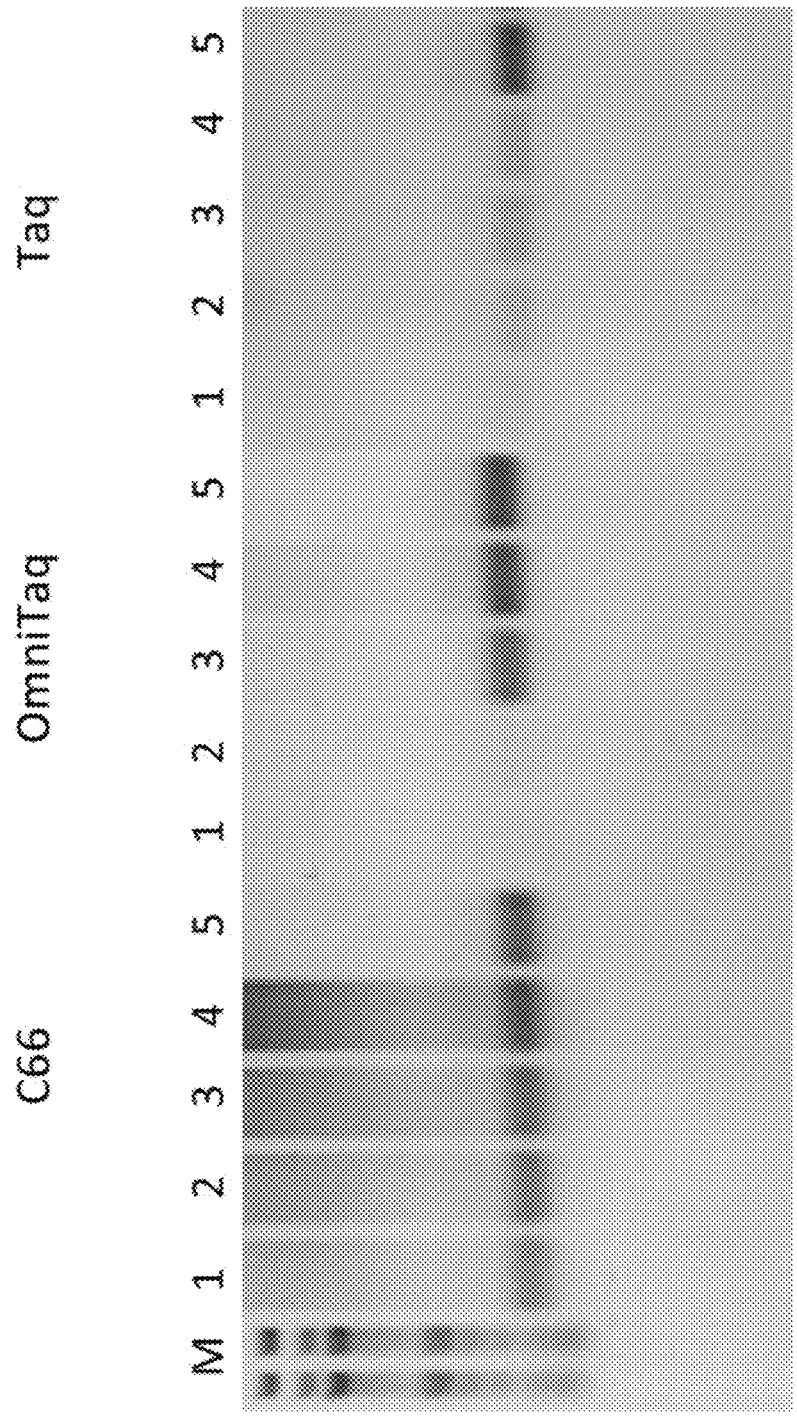
FIG. 12 is an image of a gel showing resistance of full-length Taq mutant C-66 (SEQ ID NO: 11) to shrimp meat inhibition. A 250 bp 16S rRNA target was amplified in 25 ul reactions from 1 ng *Listeria* DNA with 0.5 μl purified OmniTaq, C-66 (SEQ ID NO: 11) mutant, and wild type Taq (NEB) in the presence of 20%, 10%, 5%, 2.5% or 0% shrimp meat homogenate (Lanes 1-5). Further details regarding methodology are available in Example 12.

A 250 bp 16S rRNA target was amplified in 25 ul reactions from 1 ng Listeria DNA with 0.5 µl purified OmniTaq, C-66 (SEQ ID NO: 11) mutant, and plain Taq (NEB) in the presence of 20%, 10%, 5%, 2.5% or 0% shrimp meat homogenate (see e.g., FIG. 12, lanes 1-5).

Results showed that the C-66 (SEQ ID NO: 11) mutant polymerase had some activity at all tested concentrations while OmniTaq was clearly inhibited at 10% or above. Taq began showing inhibition at 2.5%.

Example 13

The following example shows resistance of full-length Taq mutant C-12 (SEQ ID NO: 10) to food inhibition.

Figure 13:
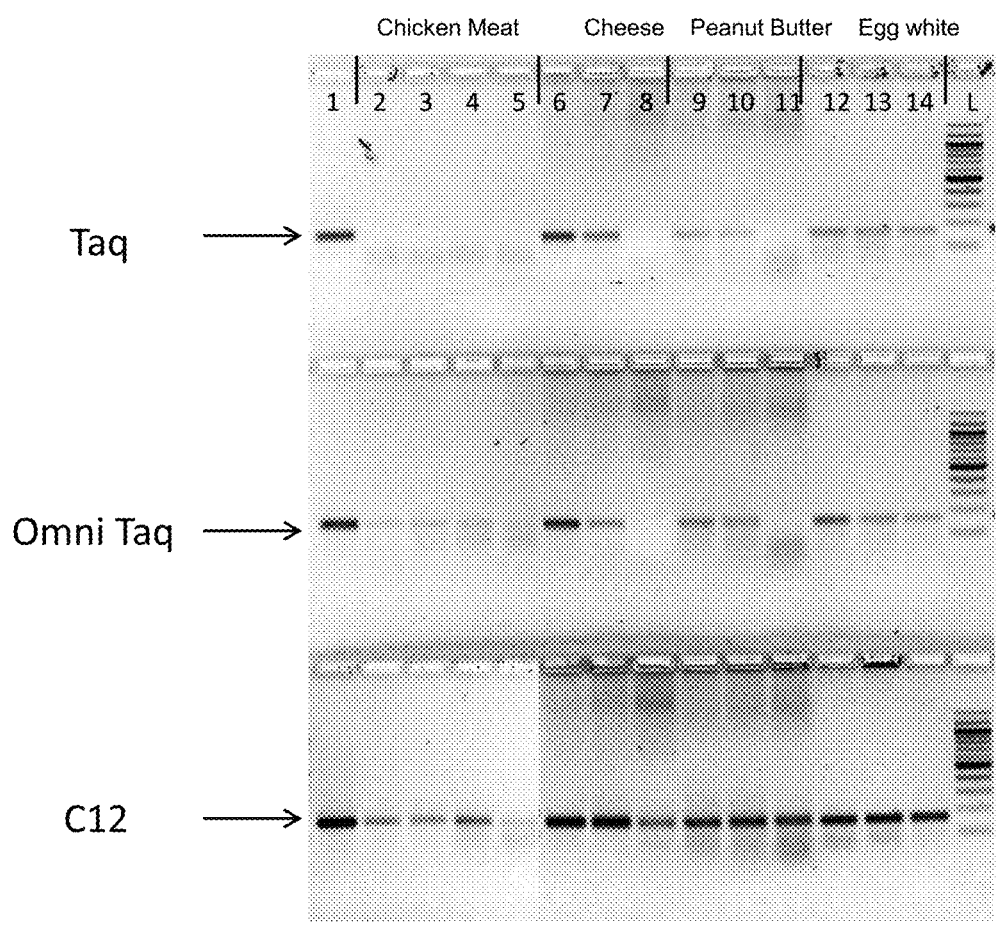
FIG. 13 is a series of gel images showing resistance of full-length Taq mutant C-12 (SEQ ID NO: 10) to food inhibition. A 170 bp 16S rRNA target was amplified in 25 ul reactions from 1.4 ng of *Salmonella* DNA with 0.3 μl of purified OmniTaq, mutant C-12 (SEQ ID NO: 10) polymerase, or an equivalent amount of wild type Taq (NEB) activity with 0 (lane 1), 2.25 μl (lane 2), 4.5 μl (lanes 3, 6, 9, 12), 9 μl (lanes 4, 7, 10, 13 or 18 μl (5, 8, 11, 14) of 10% (w/v) food extract. Further details regarding methodology are available in Example 13.

A 170 bp 16S rRNA target was amplified in 25 ul reactions from 1.4 ng of Salmonella DNA with 0.3 µl of purified OmniTaq, mutant C-12 (SEQ ID NO: 10) polymerase, or an equivalent amount of wild type Taq (NEB) activity with 0, 2.25 µl, 4.5 µl, 9 µl, or 18 µl of 10% (w/v) food extract (see e.g., FIG. 13).

Results showed that the Taq mutant C-12 (SEQ ID NO: 10) polymerase showed greater resistance to tested food samples than wild type Taq or OmniTaq.

What is claimed is:

1. An isolated DNA polymerase comprising a polypeptide sequence having at least 95% sequence identity to positions 279 through 832 of SEQ ID NO: 1, and further comprising one or more amino acid substitutions, wherein the one or more amino acid substitutions are selected from the group consisting of:
   (a) R487G;
   (b) G418E, E626K, I707L, and E708S;
   (c) L533R;
   (d) D551G, I599V, and L657Q;
   (e) E818V; and
   (f) V453L, A454S, I528M, and K738R
   wherein all amino acid substitutions are relative to SEQ ID NO: 1.

2. The isolated DNA polymerase of claim 1, further comprising one or more additional amino acid substitutions selected from the group consisting of E404G, G418E, V453L, A454S, R487G, I528M, D551G, L533R, D578E, I599V, L609P, E626K, V649I, L657Q, I707L, E708K, E708L, E708N, E708Q, E708I, E708W, E708R, E708V, E708S, D732N, K738R, L781I, and E818V; wherein all amino acid substitutions are relative to SEQ ID NO: 1.

3. The isolated DNA polymerase of claim 1, wherein the polypeptide comprises SEQ ID NO: 11.

4. The isolated DNA polymerase of claim 1, comprising SEQ ID NO: 5 (mutant B-9), SEQ ID NO: 6 (mutant H-10), SEQ ID NO: 7 (mutant F-12), SEQ ID NO: 10 (mutant C-12), SEQ ID NO: 11 (mutant C-66), or SEQ ID NO: 14 (mutant H-101).

5. The isolated DNA polymerase of claim 1, comprising SEQ ID NO: 5 (mutant B-9); or a polypeptide sequence at least 95% identical to SEQ ID NO: 5 that comprises the amino acid substitution of R487G relative to SEQ ID NO: 1.

6. The isolated DNA polymerase of claim 1, comprising SEQ ID NO: 6 (mutant H-10); or a polypeptide sequence at least 95% identical to SEQ ID NO: 6 that also comprises the amino acid substitutions of G418E, E626K, I707L, and E708S relative to SEQ ID NO: 1.

7. The isolated DNA polymerase of claim 1, comprising SEQ ID NO: 7 (mutant F-12); or a polypeptide sequence at least 95% identical to SEQ ID NO: 7 that also comprises the amino acid substitution of L533R relative to SEQ ID NO: 1.

8. The isolated DNA polymerase of claim 1, comprising SEQ ID NO: 10 (mutant C-12); or a polypeptide sequence at least 95% identical to SEQ ID NO: 10 that also comprises the amino acid substitutions of D551G, I599V, and L657Q relative to SEQ ID NO: 1.

9. The isolated DNA polymerase of claim 1, comprising SEQ ID NO: 11 (mutant C-66); or a polypeptide sequence at least 95% identical to SEQ ID NO: 11 that also comprises the amino acid substitution of E818V relative to SEQ ID NO: 1.

10. The isolated DNA polymerase of claim 1, comprising SEQ ID NO: 14 (mutant H-101); or a polypeptide sequence at least 95% identical to SEQ ID NO: 14 that also comprises the amino acid substitutions of V453L, A454S, I528M, and K738R relative to SEQ ID NO: 1.

11. A method of amplifying a target nucleic acid in a polymerase chain reaction (PCR) comprising:

forming an assay mixture comprising
  a sample comprising a target nucleic acid,
  primers specific for the target nucleic acid,
  a buffer, and
  at least one DNA polymerase of claim 1;
and
amplifying the target nucleic acid in the assay mixture in a PCR.

12. The method of claim 11, wherein the sample comprises an inhibitory substance in an amount sufficient to cause a wild type Taq polymerase comprising SEQ ID NO: 1 to fail to amplify the target nucleic acid in the PCR, wherein the inhibitory substance is selected from the group consisting of chocolate, black pepper, guanidinium thiocyanate (GITC), ethanol, blood, a blood fraction, humic acid, bile, and plant material.

13. The method of claim 11, wherein
the PCR is a real-time PCR;
the assay mixture further comprises at least one dye; and
amplifying the target nucleic acid comprises amplifying the target nucleic acid in the assay mixture in a real-time PCR.

14. A nucleic acid encoding the isolated DNA polymerase of claim 1.

15. A kit comprising the isolated DNA polymerase of claim 1.

16. An isolated DNA polymerase comprising a polypeptide sequence having at least 95% sequence identity to positions 279 through 832 of SEQ ID NO: 1, and further comprising an E818V amino acid substitution, wherein the amino acid substitution is relative to SEQ ID NO: 1.

17. An isolated DNA polymerase comprising a polypeptide sequence having at least 95% sequence identity to positions 279 through 832 of SEQ ID NO: 1, and further comprising an R487G amino acid substitution, wherein the amino acid substitution is relative to SEQ ID NO: 1.

18. The isolated DNA polymerase of claim 1, wherein the polypeptide sequence has at least 95% identity to SEQ ID NO: 1.

19. The isolated DNA polymerase of claim 1, further comprising one or more additional amino acid substitutions selected from the group consisting of E404G, L609P, V649I, E708K, E708L, E708N, E708Q, E708I, E708W, E708R, and E708V; wherein all amino acid substitutions are relative to SEQ ID NO: 1.

20. The isolated DNA polymerase of claim 1, wherein the one or more amino acid substitutions are selected from the group consisting of:
  (a) R487G;
  (b) L533R;
  (c) D551G, I599V, and L657Q;
  (d) E818V; and
  (e) V453L, A454S, I528M, and K738R;
and wherein the isolated DNA polymerase further comprises one or more additional amino acid substitutions selected from E626K and I707L.

* * * * *